United States Patent
Diep et al.

(10) Patent No.: US 12,391,658 B2
(45) Date of Patent: Aug. 19, 2025

(54) SULFOXIDE AND SULFONE GLUCOKINASE ACTIVATORS AND METHODS OF USE THEREOF

(71) Applicant: vTv Therapeutics LLC, High Point, NC (US)

(72) Inventors: Nhut Diep, Houston, TX (US); Philippe Pitchen, Genolhac (FR); Matthew Ronsheim, Sudbury, MA (US)

(73) Assignee: VTV THERAPEUTICS LLC, High Point, NC (US)

( * ) Notice: Subject to any disclaimer, the term of this patent is extended or adjusted under 35 U.S.C. 154(b) by 533 days.

(21) Appl. No.: 17/760,218

(22) PCT Filed: Feb. 12, 2021

(86) PCT No.: PCT/US2021/017743
§ 371 (c)(1),
(2) Date: Aug. 5, 2022

(87) PCT Pub. No.: WO2021/167840
PCT Pub. Date: Aug. 26, 2021

(65) Prior Publication Data
US 2023/0106983 A1    Apr. 6, 2023

Related U.S. Application Data

(60) Provisional application No. 62/977,873, filed on Feb. 18, 2020.

(51) Int. Cl.
C07D 277/54    (2006.01)
(52) U.S. Cl.
CPC .................................. C07D 277/54 (2013.01)
(58) Field of Classification Search
CPC .................................................. C07D 277/54
See application file for complete search history.

(56) References Cited

U.S. PATENT DOCUMENTS

| | | |
|---|---|---|
| 3,067,250 A | 12/1962 | Oja |
| 3,152,136 A | 10/1964 | Harris et al. |
| 3,317,534 A | 5/1967 | Yoshihiro et al. |
| 3,424,762 A | 1/1969 | Helsley et al. |
| 3,551,442 A | 12/1970 | Guillot et al. |
| 3,734,923 A | 5/1973 | Dowding et al. |
| 3,862,163 A | 1/1975 | Boroschewski et al. |
| 3,874,873 A | 4/1975 | Volpp et al. |
| 3,887,709 A | 6/1975 | Brzozowski et al. |
| 3,957,853 A | 5/1976 | Bohuon |
| 3,967,950 A | 7/1976 | Kano et al. |
| 4,153,710 A | 5/1979 | Brzozowski et al. |
| 4,160,833 A | 7/1979 | Diel |
| 4,174,398 A | 11/1979 | Frohberger et al. |
| 4,175,081 A | 11/1979 | Driscoll |
| 4,183,856 A | 1/1980 | Makisumi et al. |
| 4,241,072 A | 12/1980 | Bolhofer |
| 4,243,404 A | 1/1981 | Krueger et al. |
| 4,405,644 A | 9/1983 | Kabbe et al. |
| 4,694,004 A | 9/1987 | Nakaguti et al. |
| 4,808,722 A | 2/1989 | Henrie, II |
| 5,262,415 A | 11/1993 | Takemoto et al. |
| 5,371,086 A | 12/1994 | Takemoto et al. |
| 5,552,160 A | 9/1996 | Liversidge et al. |
| 5,556,969 A | 9/1996 | Chambers et al. |
| 5,846,985 A | 12/1998 | Murugesan |
| 5,846,990 A | 12/1998 | Murugesan et al. |
| 5,849,732 A | 12/1998 | Suzuki et al. |
| 5,849,769 A | 12/1998 | Lind et al. |

(Continued)

FOREIGN PATENT DOCUMENTS

| | | |
|---|---|---|
| AU | 2993771 A | 12/1972 |
| CA | 2416229 A1 | 1/2002 |

(Continued)

OTHER PUBLICATIONS

Agiostratidou et al., Standardizing Clinically Meaningful Outcome Measure Beyond . . . and the T1D Exchange. Diabetes Care 40:1622-1630 (2017).
Agius et al. Regulation of glycogen synthesis from glucose and gluconeogenic precursors by insulin in periportal and perivenous rat hepatocytes. Biochem J. 266:91-102 (1990).
Aicher et al. ARRY-403, A Novel Glucokinase Activator . . . Activity in Animal Models of Type 2 Diabetes Mellitus. Poster 126—Keystone Symposium: Type 2 Diabetes and Insulin Resistance (J3), Jan. 20-25, 2009, Banff, AB (Array Biopharma).
Amendment No. 6 to Form S-1 Registration Statement for vTv Therapeutics Inc.. Jul. 24, 2015. pp. 2-3, 84, 96-99.
American Diabetes Association. Classification and Diagnosis of Diabetes: Standards of Medical Care in Diabetes—2018. Diabetes Care 41(Suppl. 1):513-527 (2018).

(Continued)

*Primary Examiner* — Kamal A Saeed
(74) *Attorney, Agent, or Firm* — WILSON SONSINI GOODRICH & ROSATI

(57) ABSTRACT

This application relates to sulfoxide and sulfone compounds of Formula (X) and other compounds that may be useful to activate glucokinase as part of a treatment for various diseases including diabetes. Further encompassed are pharmaceutical compositions comprising a compound according to the invention.

Formula (X)

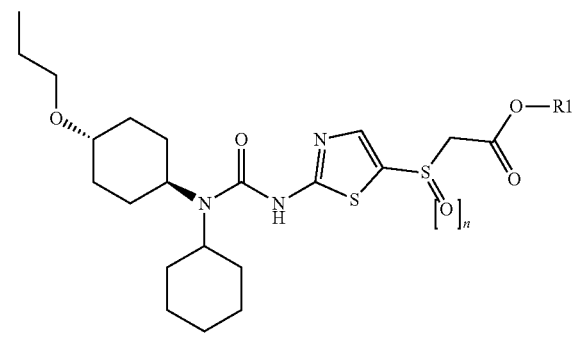

17 Claims, No Drawings

(56) References Cited

U.S. PATENT DOCUMENTS

| | | |
|---|---|---|
| 5,891,917 A | 4/1999 | Tang et al. |
| 5,935,993 A | 8/1999 | Tang et al. |
| 6,001,860 A | 12/1999 | Hamanaka |
| 6,140,343 A | 10/2000 | Deninno et al. |
| 6,180,635 B1 | 1/2001 | Cheshire et al. |
| 6,225,346 B1 | 5/2001 | Tang et al. |
| 6,268,384 B1 | 7/2001 | Novak et al. |
| 6,271,248 B1 | 8/2001 | Murugesan et al. |
| 6,337,338 B1 | 1/2002 | Kozlowski et al. |
| 6,384,220 B2 | 5/2002 | Corbett et al. |
| 6,448,290 B1 | 9/2002 | Ohuchida et al. |
| 6,486,184 B2 | 11/2002 | Kester et al. |
| 6,489,478 B1 | 12/2002 | Deninno et al. |
| 6,500,817 B1 | 12/2002 | Fischer et al. |
| 6,559,168 B2 | 5/2003 | Marfat et al. |
| 6,608,218 B2 | 8/2003 | Kester et al. |
| 6,660,716 B1 | 12/2003 | Yakubu-Madus et al. |
| 6,720,347 B2 | 4/2004 | Rawlins et al. |
| 6,720,427 B2 | 4/2004 | Sanner et al. |
| 6,784,198 B1 | 8/2004 | Pevarello et al. |
| 6,794,412 B1 | 9/2004 | Wong |
| 6,863,647 B2 | 3/2005 | Pevarello et al. |
| 6,875,760 B2 | 4/2005 | Lau et al. |
| 6,903,125 B2 | 6/2005 | Kontani et al. |
| 6,916,814 B2 | 7/2005 | Moss et al. |
| 6,936,629 B2 | 8/2005 | Chan et al. |
| 6,949,510 B2 | 9/2005 | Rosen et al. |
| 7,056,942 B2 | 6/2006 | Hildesheim et al. |
| 7,196,104 B2 | 3/2007 | Askew, Jr. et al. |
| 7,384,967 B2 | 6/2008 | Polisetti et al. |
| 7,432,287 B2 | 10/2008 | Iino et al. |
| 7,582,769 B2 | 9/2009 | Murray et al. |
| 7,598,391 B2 | 10/2009 | Murray et al. |
| 7,851,636 B2 | 12/2010 | Murray et al. |
| 7,872,139 B2 | 1/2011 | Murray et al. |
| 7,884,210 B2 | 2/2011 | Lau et al. |
| 7,897,628 B2 | 3/2011 | Polisetti et al. |
| 8,063,081 B2 | 11/2011 | Polisetti et al. |
| 8,263,634 B2 | 9/2012 | Murray et al. |
| 8,283,834 B2 | 10/2012 | Matsubara et al. |
| 8,318,778 B2 | 11/2012 | Murray et al. |
| 8,362,049 B2 | 1/2013 | Murray et al. |
| 8,586,614 B2 | 11/2013 | Lau et al. |
| RE45,183 E | 10/2014 | Murray et al. |
| RE45,670 E | 9/2015 | Polisetti et al. |
| 9,359,313 B2 | 6/2016 | Mjalli et al. |
| 9,855,251 B2 | 1/2018 | Mjalli et al. |
| 10,004,782 B2 | 6/2018 | Valcarce et al. |
| 10,064,846 B2 | 9/2018 | Mjalli et al. |
| 10,363,244 B2 | 7/2019 | Mjalli et al. |
| 10,588,943 B2 | 3/2020 | Valcarce et al. |
| 10,952,993 B2 | 3/2021 | Freeman et al. |
| 10,980,861 B2 | 4/2021 | Valcarce et al. |
| 2002/0002190 A1 | 1/2002 | Corbett et al. |
| 2002/0065239 A1 | 5/2002 | Caplan et al. |
| 2002/0198200 A1 | 12/2002 | Kester et al. |
| 2003/0171411 A1 | 9/2003 | Kodra et al. |
| 2003/0220350 A1 | 11/2003 | Lau et al. |
| 2004/0014789 A1 | 1/2004 | Lau et al. |
| 2004/0014968 A1 | 1/2004 | Bizzarro et al. |
| 2006/0246141 A1 | 11/2006 | Liversidge et al. |
| 2006/0248141 A1 | 11/2006 | Mukherjee |
| 2007/0054897 A1 | 3/2007 | Murray et al. |
| 2008/0026987 A1 | 1/2008 | Mackay et al. |
| 2008/0319028 A1 | 12/2008 | Murray et al. |
| 2009/0105482 A1 | 4/2009 | Lau et al. |
| 2009/0118501 A1 | 5/2009 | Murray et al. |
| 2009/0216013 A1 | 8/2009 | Murray et al. |
| 2009/0286800 A1 | 11/2009 | Cheruvallath et al. |
| 2010/0028439 A1 | 2/2010 | Jenkins et al. |
| 2010/0204288 A1 | 8/2010 | Murray et al. |
| 2011/0301158 A1 | 12/2011 | Polisetti et al. |
| 2011/0313007 A1 | 12/2011 | Mjalli et al. |
| 2012/0071404 A1 | 3/2012 | Tucker |
| 2014/0066372 A1 | 3/2014 | Valcarce Lopez et al. |
| 2016/0015638 A1 | 1/2016 | Mo et al. |
| 2016/0015816 A1 | 1/2016 | Benjamin et al. |
| 2016/0184277 A1 | 6/2016 | Mjalli et al. |
| 2018/0311314 A1 | 11/2018 | Valcarce Lopez et al. |
| 2019/0046645 A1 | 2/2019 | Benjamin et al. |
| 2019/0328713 A1 | 10/2019 | Chen et al. |
| 2021/0169857 A1 | 6/2021 | Freeman et al. |
| 2021/0169858 A1 | 6/2021 | Freeman et al. |
| 2022/0233701 A1 | 7/2022 | Benjamin et al. |
| 2023/0219909 A1 | 7/2023 | Teng et al. |
| 2023/0219910 A1 | 7/2023 | Teng et al. |
| 2024/0245656 A1 | 7/2024 | Freeman et al. |

FOREIGN PATENT DOCUMENTS

| | | |
|---|---|---|
| CA | 2724116 A1 | 11/2009 |
| DE | 1901501 A1 | 8/1969 |
| DE | 2040580 A1 | 4/1971 |
| DE | 2117807 A1 | 10/1971 |
| DE | 2129418 A1 | 12/1971 |
| DE | 2228890 A1 | 12/1972 |
| DE | 2151766 A1 | 4/1973 |
| DE | 2357875 A1 | 9/1974 |
| DE | 2264983 A1 | 10/1975 |
| EP | 0129408 A2 | 12/1984 |
| EP | 0432040 A1 | 6/1991 |
| EP | 0499299 A2 | 8/1992 |
| EP | 0885890 A1 | 12/1998 |
| EP | 0979823 A1 | 2/2000 |
| EP | 1125922 A1 | 8/2001 |
| EP | 1211246 A1 | 6/2002 |
| EP | 2392575 A1 | 12/2011 |
| FR | 7428 M | 11/1969 |
| GB | 771147 A | 3/1957 |
| GB | 1185540 A | 3/1970 |
| GB | 1195672 A | 6/1970 |
| GB | 1260386 A | 1/1972 |
| GB | 1282308 A | 7/1972 |
| GB | 1318291 A | 5/1973 |
| JP | S6456660 A | 3/1989 |
| JP | 4334374 B2 | 9/2009 |
| JP | 6016621 B2 | 10/2016 |
| JP | 6102611 B2 | 3/2017 |
| RU | 2021258 C1 | 10/1994 |
| WO | WO-9104027 A1 | 4/1991 |
| WO | WO-9324458 A1 | 12/1993 |
| WO | WO-9414801 A1 | 7/1994 |
| WO | WO-9418170 A1 | 8/1994 |
| WO | WO-9724328 A1 | 7/1997 |
| WO | WO-9924035 A1 | 5/1999 |
| WO | WO-9924416 A1 | 5/1999 |
| WO | WO-9932106 A1 | 7/1999 |
| WO | WO-9932111 A1 | 7/1999 |
| WO | WO-9962890 A1 | 12/1999 |
| WO | WO-0017165 A1 | 3/2000 |
| WO | WO-0026186 A1 | 5/2000 |
| WO | WO-0026203 A1 | 5/2000 |
| WO | WO-0045742 A1 | 8/2000 |
| WO | WO-0053591 A1 | 9/2000 |
| WO | WO-0058293 A2 | 10/2000 |
| WO | WO-0100206 A1 | 1/2001 |
| WO | WO-0144216 A1 | 6/2001 |
| WO | WO-0144217 A1 | 6/2001 |
| WO | WO-0157008 A1 | 8/2001 |
| WO | WO-0183465 A2 | 11/2001 |
| WO | WO-0183478 A2 | 11/2001 |
| WO | WO-0185706 A1 | 11/2001 |
| WO | WO-0185707 A1 | 11/2001 |
| WO | WO-0208209 A1 | 1/2002 |
| WO | WO-0214311 A2 | 2/2002 |
| WO | WO-0246173 A1 | 6/2002 |
| WO | WO-02070494 A1 | 9/2002 |
| WO | WO-03055482 A1 | 7/2003 |
| WO | WO-03070727 A1 | 8/2003 |
| WO | WO-2004002481 A1 | 1/2004 |
| WO | WO-2004085388 A2 | 10/2004 |
| WO | WO-2005023706 A2 | 3/2005 |
| WO | WO-2005023766 A1 | 3/2005 |
| WO | WO-2005066145 A1 | 7/2005 |

(56) References Cited

FOREIGN PATENT DOCUMENTS

| | | |
|---|---|---|
| WO | WO-2005086145 A1 | 9/2005 |
| WO | WO-2005103050 A2 | 11/2005 |
| WO | WO-2005123132 A2 | 12/2005 |
| WO | WO-2007006760 A1 | 1/2007 |
| WO | WO-2007006814 A1 | 1/2007 |
| WO | WO-2008079787 A2 | 7/2008 |
| WO | WO-2008084043 A1 | 7/2008 |
| WO | WO-2008084044 A1 | 7/2008 |
| WO | WO-2009140624 A2 | 11/2009 |
| WO | WO-2009140824 A1 | 11/2009 |
| WO | WO-2010107610 A1 | 9/2010 |
| WO | WO-2010119990 A1 | 10/2010 |
| WO | WO-2011025270 A2 | 3/2011 |
| WO | WO-2011149945 A1 | 12/2011 |
| WO | WO-2013173417 A2 | 11/2013 |
| WO | WO-2014137797 A2 | 9/2014 |
| WO | WO-2014137799 A1 | 9/2014 |
| WO | WO-2018005707 A1 | 1/2018 |
| WO | WO-2019241089 A1 | 12/2019 |
| WO | WO-2021167840 A1 | 8/2021 |
| WO | WO-2021252309 A1 | 12/2021 |
| WO | WO-2021252311 A1 | 12/2021 |

OTHER PUBLICATIONS

Annals of Internal Medicine, Health Implications of Obesity, Bethesda, Maryland, 103:147-151 (1985).
Asfari et al. Establishment of 2-mercaptoethanol-dependent differentiated insulin-secreting cell lines. Endocrinology 130:167-178 (1992).
Atwal et al., Cardioselective Antiischemic Atp-Sensitive Potassium Channel Openers 4 Structure-Activity Studies on Benzopyranylcyanoguanidines: Replacement of the Benzopyran Portion. Journal of Medicinal Chemistry 39:304-313 (1996).
Bank et al. Prevention of duodenal ulcers in the rat using a combination of ranitidine and sucralphate in subtherapeutic doses. Gut 26:603-606 (1985).
Battelino et al. Clinical Targets for Continuous Glucose Monitoring Data. Diabetes Care 42:1593-1603 (2019).
Berge et al. Pharmaceutical Salts. Journal of Pharmaceutical Sciences 66(1):1-19 (Jan. 1977).
Bonadonna et al. Piragliatin (RO4389620), a Novel Glucokinase Activator, Lowers Plasma Glucose Both in the Postabsorptive State and after a Glucose Challenge in Patients with Type 2 Diabetes Mellitus: A Mechanistic Study. J Clin Endocrinol Metab, 95(11):1-9 (2010).
Buse et al. Simplici-T1 First Clinical Trial to Test Activation of Glucokinase as an Adjunctive Treatment for Type 1 Diabetes. Diabetes 67 (Supplement_1): 126-LB (Abstract) (Mar. 2018).
Buse et al. Simplici-T1: First Clinical Trial to Test Activation of Glucokinase as an Adjunctive Treatment for Type 1 Diabetes Poster presented at the 78th Scientific Session of ADA in Orlando, FL, Jun. 22-26, 2018.
Buse et al. The Simplici-TI Trial: Glucokinase activator (GKA) TTP399 improves glycemic control in patients with type 1 diabetes (T1D) Poster presented at the 80th Scientific Session of ADA, Jun. 12-16, 2020.
Castelhano et al., Glucokinase-activating ureas. Bioorg Med Chem Lett 15:1501-1504 (2005).
Chipkin et al., Joslin's Diabetes, pp. 97-115 (1994).
ClinicalTrials.gov—Clinical Trials Identifier NCT01247363 (2011).
Colowick., The Hexokinases. The Enzymes 9:1-48 (1973).
Danne et al. International Consensus on Use of Continuous Glucose Monitoring. Diabetes Care 40:1631-1640 (2017).
Database WPI Week 201123, Thomson Scientific, London, GB; AN 2011-C11325 & WO 2011/025270 A2 (Haneli Biopharma Co Ltd) Mar. 3, 2011 (Mar. 3, 2011).
Davidson et al. Exenatide. Nat Rev Drug Discov 4:713-714 (Sep. 2005).
Decombe et al., Acylacetic esters. Annual of Chem App. 18:81-187 (1932).
Dhanesha et al. Treatment with exendin-4 improves the antidiabetic efficacy and reverses hepatic steatosis in glucokinase activator treated db/db mice. Eur J Pharmacol 714:188-192 (2013).
Di Marco et al. Synergistic effect of deoxyspergualin (DSP) and cyclosporin A (CsA) in the prevention of spontaneous autoimmune diabetes in BB rats. Clin Exp Immunol 105:338-343 (1996).
Diabetes 2, 2011, http://www.mayoclinic.com/health/type-2-diabetes/DS00585.
Diabetes 2-2, 2011, http://www.mayoclinic.com/health/type-2-diabetes/DS00585/DSECTION=prevention.
Doliba et al. Glucokinase activation repairs defective bioenergetics of islets of Langerhans isolated from type 2 diabetics. Am. J. Physiol. Endocrinol. Metab. 302:E87-E102 (2011).
Drucker et al. Sitagliptin. Nat Rev Drug Discov 6:109-110 (2007).
Eiki et al. Pharmacokinetic and Pharmacodynamic Properties of the Glucokinase Activator MK-0941 in Rodent Models of Type 2 Diabetes and Healthy Dogs. Mol Pharmacol 80:1156-1165 (2011).
Ericsson et al. The glucokinase activator AZD6370 decreases fasting and postprandial glucose in type 2 diabetes mellitus patients with effects influenced by dosing regimen and food. Diabetes Research and Clinical Practice 98:436-444 (2012).
Evans et al., Design of potent, orally effective, nonpeptidal antagonists of the peptide hormone cholecystokinin. PNAS USA 83(13):4918-4922 (1986).
Ferre et al., Evidence from transgenic mice that glucokinase is rate limiting for glucose utilization in the liver. The Faseb Journal 10:1213-1218 (1996).
Freeman et al. Mechanism matters: preliminary evidence that activation of glucokinase by TTP399 does not increase plasma or urine ketones in type 1 diabetes, P51, presented at the 56th European Association for the Study of Diabetes Conference—Virtual, Sep. 22, 2020.
Gardner., Studies In The Polyoxyphenol Series: Iii. Syntheses of Substituted Phenylureas From Methylated and Ethylated Vanillin. Canadian Journal Research 26:681-693 (1948).
Garg et al. Effects of Sotagliflozin Added to Insulin in Patients with Type 1 Diabetes. N Engl J Med 377:2337-48 (2017).
Girard et al., Mechanisms by which carbohydrates regulate expression of genes for glycolytic and lipogenic enzymes. Annu Rev Nutr 17:325-352 (1997).
Glaser et al., Familial hyperinsulinism caused by an activating glucokinase mutation. N Engl J Med 338:226-230 (1998).
Goerdeler et al., Acylcarbodiimides. Iv. Preparation and Some Reactions of Carbamoylcarboiimides, Hcaplus, Accession No. 585914 (1980).
Grupe et al., Transgenic knockouts reveal a critical requirement for pancreatic beta cell glucokinase in maintaining glucose homeostasis. Cell 83:69-78 (1995).
Gude D., Red carpeting the newer antidiabetics. J Pharmacol Pharmacother. 3(2):127-131 (2012).
Guidance for Industry, Estimating the Maximum Safe Starting Does in Initial Clinical Trials for Therapeutics in Adult Healthy Volunteers, FDA. Jul. 2005 activity in animal modest of type 2 diabetes mellitus. Diabetologia 52(Suppl):S342 (2009).
Heitmeier et al., Hydroxyphenethylamino Derivatives of Various Nitrogen Heterocycles. J Med Chem 7(3):288-293 (1964).
Hinklin et al. ARRY-403, a glucokinase activator with potent glucose-dependent anti-hyperglycaemic activity in animal models of type 2 diabetes mellitus. Diabetologia 52(Supp):S342 (2009).
Investor Presentation—Jul. 2015. Slides 19-23.
Johnson et al. Glucose-dependent modulation of insulin secretion and intracellular calcium ions by GKA50, a glucokinase activator. Diabetes 56:1694-1702 (2007).
Kos et al., New treatments for type 2 diabetes. J.R.Coll. Physicians Edinb. 39(3):227-230 (2009).
Li et al. The Effect of the Physical States of Binders on High-Shear Wet Granulation and Granule Prop-erties: A Mechanistic Approach Toward Understanding High-Shear Wet Granulation Process. Part II. Granulation and Granule Properties. J Pharm Sci 100:294-310 (2011).

(56) References Cited

OTHER PUBLICATIONS

Liang et al., Variable effects of maturity-onset-diabetes-of-youth (MODY)-associated glucokinase mutations on substrate interactions and stability of the enzyme. Biochem Journal 309:167-173 (1995).
Lin et al. Development of potential novel cushioning agents for the compaction of coated multi-particulates by co-processing micronized lactose with polymers. Eur J Pharm Biopharm 79(2):406-179:406-415 (2011).
Lindstrom. The Physiology of Obese-Hyperglycemic Mice [ob/ob Mice] Scientific World Journal 7:666-685 (2007).
Lu et al. Characterization of a Novel Glucokinase Activator in Rat and Mouse Models. PLoS One 9(2):88431 (2014).
Mann. The Influence of Obesity on Health. N Engl J Med 291:226-232 (1974).
Mathieu et al. Glucose Variable in Type 1 Diabetes Studies With Dapagliflozin: Pooled Analysis of Continuous Glucose Monitoring Data From DEPICT-1 and 2, Diabetes Care 42:1081-1087 and supplementary data (2019).
Matschinsky et al. Glucokinase activators for diabetes therapy: May 2010 status report. Diabetes Care 34(Suppl 2):S236-S243 (2011).
Matschinsky et al. Research and Development of Glucokinase Activators for Diabetes Therapy: Theoretical and Practical Aspects. Handb Exp Pharmacol 203:357-401 (2011).
Matschinsky. GKAs for diabetes therapy: why No. clinically useful drug after two decades of trying? Trends Pharmacol Sci 34(2):90-9 (2013).
McCarty. In type 1 diabetics, high-dose biotin may compensate for low hepatic insulin exposure, promoting a more normal expression of glycolytic and gluconeogenic enzymes and thereby aiding glycemic control. Medical Hypotheses 95:45-8 (2016).
McVean et al., Combination Therapy of ARRY-403 with Metformin. Sitagliptin or Pioglitazone Results in Additive Glucose Lowering in Female ZDF Rats, Poster 104—Keystone Symposium! Type 2 Diabetes and Insulin Resistance (J3), Jan. 20-25, 2009, Banff, AB (Array Biopharma).
Meglasson et al., New perspectives on pancreatic islet glucokinase. Am J Physiol 246:E1-E13 (1984).
Migoya et al. The Glucokinase (GK) Activator MK-0599 Lowers Plasma Glucose Concentrations in Healthy Non-Diabetic Subjects. Diabetologia 52:S344-S344 Abstract (2009).
Mylari et al., Design and Synthesis of a Novel Family of Triazine-Based Inhibitors of Sorbitol Dehydrogenase With Oral Activity: 1-{4-[3r,5s-Dimethyl-4-(4-Methyl-[1,3,5]Triazin-2-Yl)-Piperazin-1-Yl]-[1,3,5]Triazin-2-YI)-(R) Ethanol. Bioorgan Med Chem 11:4179-4188 (2003).
Nakamura et al. Control of beta cell function and proliferation in mice stimulated by small-molecule glucokinase activator under various conditions. Diabetologia 55(5):1745-1754 (2012).
Nathan et al. Medical Management of Hyperglycemia in Type 2 Diabetes: A Consensus Algorithm for the Initiation and Adjustment of Therapy. Diabetes Care 32:193-203 (2009).
Newton. Chapter 12: Drug Release from Capsules. Phamaceutical Capsules, Pharmaceutical Press, Podczeck et al. Eds. 2nd Ed. (pp. 213-237) (2004).
Pal et al. Recent advances in glucokinase activators for the treatment of type 2 diabetes. Drug Discovery Today 14(15/16):784-792 (2009).
Patani et al. Bioisosterism: A Rational Approach in Drug Design. Chem. Rev. 96:3147-3176 (1996).
PCT/US2019/036227 International Search Report and Written Opinion dated Nov. 5, 2019.
PCT/US2021/017743 International Search Report and Written Opinion dated Apr. 21, 2021.
PCT/US2021/036082 International Search Report and Written Opinion dated Sep. 8, 2021.
PCT/US2021/036084 International Search Report and Written Opinion dated Sep. 9, 2021.
Pfefferkom. Strategies for the design of hepaloselective glucokinase activators to treat type 2 diabetes. Expert Opin. Drug Discov. 8(3):319-330 (2013).
Pfuetzner et al. Intensive insulin therapy with insulin lispro in patients with type 1 diabetes reduces the frequency of hypoglycemic episodes. Exp Clin Endocrinol Diabetes 104(1):25-30 (abstract) (1996).
Polakof. Diabetes Therapy: Novel Patents Targeting the Glucose-Induced Insulin Secretion. Recent Pat DNA Gene Seq 4(1):1-9 (2010).
Printz et al. Mammalian glucokinase. Ann Rev Nutr 13:463-496 (1993).
Priyadarsini et al. Glucokinase Activators: A Glucose Sensor Role in Pancreatic Islets and Hepatocyte. International Journal of Pharmacy and Pharmaceutical Sciences 4(2):81-87 (2012).
Purchase et al., Tetrazole-Substituted Ureas as Inhibitors of Acyl-Coa:Cholesterol O-Acyltransferase (Acat) a Novel Preparation of Ureas From Weakly Nucleophilic Amines. Biorgan Med Chem Lett 6(15):1753-1758 (1996).
Purves et al., Preliminary tests on possible new stabilizers for nitrocelluloses. Canadian Journal Research 28:468-484 (1950).
Regel et al., Acylierung An C-2 Von Imidazolen Und Benzimidazolen, Liebigs Annalen Der Chemie 1:145-158 (1977).
Ripsin et al., Management of Blood Glucose in Type 2 Diabetes Mellitus. American Family Physician 79:29-36 (Jan. 2009).
Rosenstock et al. Empagliflozin as Adjunctive to Insulin Therapy in Type 1 Diabetes: The EASE Trials. Diabetes Care 41:2560-9 (2018).
Sands et al. Sotagliflozin, a Dual SGLT1 and SGLT2 Inhibitor, as Adjunct Therapy to Insulin in Type 1 Diabetes. Diabetes Care 38(7):1181-1188 (2015).
Sands et al. Sotagliflozin, a Dual SGLT1 and SGLT2 Inhibitor, as Adjunct Therapy to Insulin in Type 1 Diabetes. Diabetes Care 38(7):1181-1188 (Supplementary Data) (2015).
Scheler. Heat Developable Diazotype Material, Hcaplus, Accession No. 444446, Nov. 5, 1968 (1969).
Sovetskaya Enthiklopedia, pp. 130-131 (1983) (with English translation).
Valcarce, C., et al., The Simplici-T1 trial: Activation of glucokinase by TTP399 improves glycemic control in patients with T1DM, P50, presented at the 56th European Association for the Study of Diabetes Conference—Virtual, Sep. 22, 2020.
Valcarce et al. TTP399, A Liver Selective Glucokinase Activator Increases Efficacy of Currently Marketed Therapies for Type 2 Diabetes. Jun. 2015. ADA 75th Scientific Sessions, Boston (Abstract 1271-P).
Valcarce et al. TTP399, a Liver-Selective Glucose Kinase Activator (GKA), Lowers Glucose and Does Not Increase Lipids in Subjects with Type 2 Diabetes Mellitus (T2DM). Jun. 2014. ADA 74th Scientific Sessions. (Abstract 122-OR).
Valcarce et al. Results from the sentinel and learning phase of the Simplici-T1 study, the first clinical trial to test activation of glucokinase as an adjunctive treatment for type 1 diabetes. Presented at the 55th EASD conference, Sep. 18, 2019, Barcelona, Spain.
Valcarce et al. The Simplici-T1 Trial: Relationship Between Glycemic Control and Insulin Dose Poster presented at the 80th Scientific Session of ADA, Jun. 12-16, 2020.
Valcarce et al. TTP399, A Liver Selective Glucokinase Activator (GKA) the Preserves the Physiological Regulation of Glucokinase (GK) by GK Regulatory Protein (GKRP). Jun. 2015. ADA 75th Scientific Sessions, Boston (Poster 1168-P).
Valcarce et al. TTP399, A Liver Selective Glucokinase Activator (GKA) the Preserves the Physiological Regulation of Glucokinase (GK) by OK Regulatory Protein (GKRP). Jun. 2015. ADA 75th Scientific Sessions. Boston (Abstract 1168-P).
Valcarce et al. TTP399. A Liver Selective Glucokinase Activator Increases Efficacy of Currently Marketed Therapies for Type 2 Diabetes. Jun. 2015. ADA 75th Scientific Sessions: Boston (Poster 1271-P).
Valcarce et al. TTP399, a Liver-Selective Glucose Kinase Activator (GKA), Lowers Glucose and Does Not Increase Lipids in Subjects with Type 2 Diabetes Mellitus (T2DM). Jun. 2014. ADA 74th Scientific Sessions. (Power Point 122-OR).

(56) References Cited

OTHER PUBLICATIONS

Valcarce et al. TTP399, a Novel, Liver Selective Glucokinase Activator: Results from a 10 day Pilot Study in Patients with type 2 Diabetes Mellitus *(T2DM) Naive to Drug, Poster presented at the 76th Scientific Sessions of the American Diabetes Association in New Orleans, LA, Jun. 11-13, 2016.

Valcarce. Selective Activation of Glucokinase (GK) in the Liver: Improves Glycemic Control and Reduces Insulin Need as Well as Risk of Ketoacidosis in Type 1 Diabetic Minipigs, presented at the Keystone Symposia on Diabetes, Jan. 22-26, 2017, Keystone, Colorado.

Valcarce. The Importance of Tissue Selectivity and Preservation of the Physiological Regulation when Targeting Key Metabolic Regulators as Glucokinase, Poster presented at the Keystone Conference in La Jolla, CA, Apr. 17-20, 2016.

Vella et al. Abstract TTP399: A liver-selective and Therapeutically Viable Glucokinase Activator . . . Study presented at the 17th Annual Rachmiel Levine-Arthur Riggs Diabetes Research Symposium, Endocrine Society ENDO2017 Conference, Orlando, Florida, Mar. 27-Apr. 4, 2017.

Vella et al. Targeting hepatic glucokinase to treat diabetes with TTP399, a hepatoselective glucokinase activator. Sci Transl Med. Jan. 16, 2019;11(475):eaau3441 (2019).

Vella et al., TTP399: A liver-selective and Therapeutically Viable Glucokinase Activator. Results from a 6-Month Phase 2 Study presented at the 17th Annual Rachmiel Levine-Arthur Riggs Diabetes Research Symposium, Endocrine Society ENDO2017 Conference, Orlando, Florida, Mar. 27-Apr. 4, 2017.

Von Herrath. Can We Learn From Viruses How to Prevent Type 1 Diabetes? The Role of Therapies. Diabetes 58:2-11 (Jan. 2009).

Wawer. Magnetic Resonance In Chemistry 37(3):189-194 (1999).

White et al. Heterocyclic Ureas: Inhibitors of Acyl-Coa: Cholesterol O-Acyltransferase as Hypocholesterolemic Agents. J Med Chem 39(22):4382-4395 (1996).

Williams-Herman et al. Safety and tolerability of sitagliptin in clinical studies: a pooled analysis of data from 10,246 patients with type 2 diabetes. BMC Endocrine Disorders 10:7 (2010).

Wolff Burger's Medical Chemistry and Drug Discovery. Principles and Practice, 1:172-178 (1995).

Wolfsdorf et al. SGLT Inhibitors for Type 1 Diabetes: Proceed with Extreme Caution, Diabetes Care 42:991-3 (2019).

Zheng et al., Exenatide sensitizes insulin-mediated whole-body glucose disposal and promotes uptake of exogenous glucose by the liver. Diabetes 58(2):352-359 (2009).

Anderson, Bradley D et al. Chapter 34: Preparation of water-soluble organic compounds by salt formation. Latest Drug Discovery Chemistry 2:347-365 (1999).

Bastin, Richard J et al. Salt Selection and Optimisation Procedures for Pharmaceutical New Chemical Entities. Organic Process Research and Development 4(5):427-435 (2000).

Braga, Dario et al. Crystal polymorphism and multiple crystal forms. Structure and Bonding 132:25-50 (2009).

Caira, Mino R. Crystalline Polymorphism of Organic Compounds. In: Design of Organic Solids, Topics in Current Chemistry. Springer 198:163-208 (1998).

Donnelly, L.A. et al., Frequency and predictors of hypoglycaemia in Type 1 and insulin-treated Type 2 diabetes: a population-based study. Diabet Med 22(6):749-755 (2005).

Hilfiker, Rolf, et al. Relevance of Solid-State Properties for Pharmaceutical Products. In: Polymorphism: In the Pharmaceutical Industry. Wiley:1-19 (2006).

Kumar, Challa V, and Anita Chaudhari. Proteins Immobilized at the Galleries of Layered a-Zirconium Phosphate: Structure and Activity Studies. Journal of the American Chemical Society 122(5):830-837 (2000).

Terada, Katsuhide. Application of Thermal Analysis to the Pharmaceutical Development. Netsu Sokutei 38(2):46-53 (2010).

Yamano, Mitsuhisa. Approach to Crystal Polymorph in Process Research of New Drug. Journal of Synthetic Organic Chemistry Japan 65(9):907-913 (2007).

Yoshinori, Nakai, and Manabu Hanano. New Pharmaceutical Science. Nanzando Co., Ltd :1-26 (1984).

Bhattacharya et al. Chapter 9: Thermoanalytical and Crystallographic Methods. Polymorphism in pharmaceutical solids. pp. 318-346 (2018).

Brittain. Polymorphism and Solvatomorphism J Pharm Sci 98(5):1617-1642 (2009).

Gabriely et al. Fructose normalizes specific counterregulatory responses to hypoglycemia in patients with type 1 diabetes. Diabetes 54(3):609-616 (2005).

Morisette et al. High-throughput crystallization: polymorphs, slats, co-crystals, and solvates of pharmaceutical solids. Advanced Drug Delivery Reviews 56:275-300 (2004).

Morral et al. Adenovirus-mediated expression of glucokinase in the liver as an adjuvant treatment for type 1 diabetes. Hum Gene Ther 12(13):1561-1570 (2002).

Meininger, Gary E. et al. Effects of MK-0941, a novel glucokinase activator, on glycemic control in insulin-treated patients with type 2 diabetes. Diabetes Care 34(12):2560-2566 (2011).

SULFOXIDE AND SULFONE GLUCOKINASE ACTIVATORS AND METHODS OF USE THEREOF

FIELD OF THE INVENTION

This application relates to glucokinase activators and their use in treatment of assorted diseases.

BACKGROUND OF THE INVENTION

Glucokinase (GK) is one of four hexokinases that are found in mammals. The hexokinases catalyze the first step in the metabolism of glucose, i.e., the conversion of glucose to glucose-6-phosphate. Glucokinase has a limited cellular distribution, being found principally in pancreatic β-cells and liver parenchymal cells. In addition, GK is a rate-controlling enzyme for glucose metabolism in these two cell types that are known to play critical roles in whole-body glucose homeostasis. An increase in glucose exposure is coupled through GK in β-cells to increased insulin secretion and in hepatocytes to increased glycogen deposition and perhaps decreased glucose production.

Compounds that activate GK and, thereby, increase the sensitivity of the GK sensor system may be useful in the treatment of diabetes, metabolic disorders, and related complications or disorders, especially the hyperglycemia characteristic of diabetes and metabolic disorders. Several GK activators have been described in the scientific literature and patent publications. See, for example, MATSCHINSKY et al., "Research and Development of Glucokinase Activators for Diabetes Therapy: Theoretical and Practical Aspects," in M. Schwanstecher (ed.), Diabetes—Perspectives in Drug Therapy, Handbook of Experimental Pharmacology 203, 2011, pp. 357-401. Also see the compounds disclosed in patent publications WO 2005/066145 and WO 2014/137799 including:

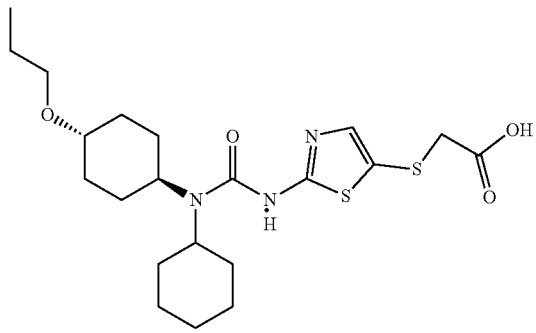

SM-1

{2-[3-Cyclohexyl-3-(trans-4-propoxy-cyclohexyl)-ureido]-thiazol-5-ylsulfanyl}-acetic acid (See Example 368 of WO 2005/066145) and pharmaceutically acceptable salts thereof. The compound {2-[3-cyclohexyl-3-(trans-4-propoxy-cyclohexyl)-ureido]-thiazol-5-ylsulfanyl}-acetic acid is referred to below as Starting Material-1 or SM-1.

SUMMARY OF THE INVENTION

The present invention provides compounds of Formula (X) and pharmaceutically acceptable salts thereof as described in the embodiments below. The present invention also provides methods for preparing such compounds.

The present invention also provides pharmaceutical compositions comprising a compound of Formula (X) and pharmaceutically acceptable salts thereof. The present invention also provides processes for preparing such pharmaceutical compositions.

The present invention also provides use of compounds of Formula (X) and pharmaceutically acceptable salts thereof for the treatment of various diseases, such as diabetes and related conditions associated with the dysregulation of glucose metabolism.

The present invention also provides use of compounds of Formula (X) and pharmaceutically acceptable salts thereof in the preparation of a medicament for the treatment of various diseases such as diabetes and related conditions associated with the dysregulation of glucose metabolism.

DETAILED DESCRIPTION OF THE INVENTION

I. Definitions

The term "treatment" and "treating" as used herein means the management and care of a subject or patient for the purpose of combating a disease, disorder or condition. The term is intended to include the full spectrum of treatments for a given disorder from which the subject or patient is suffering, such as delaying the onset of or the progression of the disease, disorder or condition, the alleviation or relief of symptoms and complications. The subject or patient to be treated is preferably a mammal, in particular a human.

The term "pharmaceutically acceptable salt" as used herein includes pharmaceutically acceptable acid addition salts, pharmaceutically acceptable base addition salts, pharmaceutically acceptable metal salts, ammonium salts, and alkylated ammonium salts. Acid addition salts include salts of inorganic acids as well as organic acids. Representative examples of suitable inorganic acids include hydrochloric, hydrobromic, hydroiodic, phosphoric, sulfuric, and nitric acids. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, and ketoglutarates. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium, zinc, and calcium salts. Examples of amines and organic amines include ammonium, methylamine, dimethylamine, trimethylamine, ethylamine, diethylamine, propylamine, butylamine, tetramethylamine, ethanolamine, diethanolamine, triethanolamine, meglumine, ethylenediamine, choline, N,N'-dibenzylethylenediamine, N-benzylphenylethylamine, N-methyl-D-glucamine, and guanidine. Examples of cationic amino acids include lysine, arginine, and histidine.

The pharmaceutically acceptable salts may be prepared by reacting the compound of the invention with a base such as sodium hydroxide, sodium methoxide, sodium hydride, potassium t-butoxide, calcium hydroxide, and magnesium hydroxide, in solvents such as ether, THF, methanol, t-butanol, dioxane, isopropanol, ethanol etc. Mixture of solvents may be used. Organic bases such as lysine, arginine, diethanolamine, choline, guanidine and their derivatives etc. may also be used. Alternatively, acid addition salts wherever applicable are prepared by treatment with acids such as hydrochloric acid, hydrobromic acid, nitric acid, sulfuric acid, phosphoric acid, p-toluenesulfonic acid, methanesulfonic acid, acetic acid, citric acid, maleic acid salicylic acid, hydroxynaphthoic acid, ascorbic acid, palmitic acid, succinic acid, benzoic acid, benzenesulfonic acid, and tartaric acid in solvents such as ethyl acetate, ether, alcohols, acetone, THF, dioxane etc. Mixture of solvents may also be used.

The term "combination therapy", "combined", "in combination with", and the like, as used herein refers to the administration of a single pharmaceutical dosage formulation which comprises the glucokinase activator compound of the present invention and another active agent(s), as well as administration of each active agent(s) in its own separate pharmaceutical dosage formulation. Where separate dosage formulations are used, the compound of the present invention and another active agent(s) can be administered to the patient at essentially the same time, i.e. concurrently, or at separate staggered times, i.e. sequentially. When given by different dosage formulations, the route of administration may be the same or different for each agent. Any route of administration known or contemplated for the individual agents is acceptable for the practice of the present invention.

The term "liver-selective glucokinase activator", and the like, as used herein refers a compound which increases glucose utilization in the liver without inducing a substantial increase in insulin secretion in response to glucose. In an embodiment, a liver-selective glucokinase activator can be viewed as a compound which shows a substantially higher activity in isolated hepatocytes compared to the activity of the compound in Ins-1 cells. In another embodiment, a liver-selective glucokinase activator can be viewed as a compound which shows a substantially higher activity in isolated hepatocytes measured as described in the Glucokinase Activity Assay (II) compared to the activity of the compound in Ins-1 cells measured as described in the Glucokinase Activity Assay (III). In another embodiment, a liver-selective glucokinase activator can be viewed as a compound which shows an activity in isolated hepatocytes measured as described in the Glucokinase Activity Assay (II) which activity is at least 1.1 fold higher, or at least 1.2 fold higher, or at least 1.3 fold higher, or at least 1.4 fold higher, or at least 1.5 fold higher, or at least 2.0 fold higher, or at least 5.0 fold higher, or at least 10 fold higher than the activity of the compound in Ins-1 cells measured as described in the Glucokinase Activity Assay (III).

The term "subject" as used herein refers to a mammal. In an embodiment, a subject may be a non-human primate, a companion animal such as a cat or dog, domesticated livestock such as a cow or horse. In another embodiment, the subject may be a human II. Compounds of Invention In one aspect, the present invention provides a compound of Formula (X):

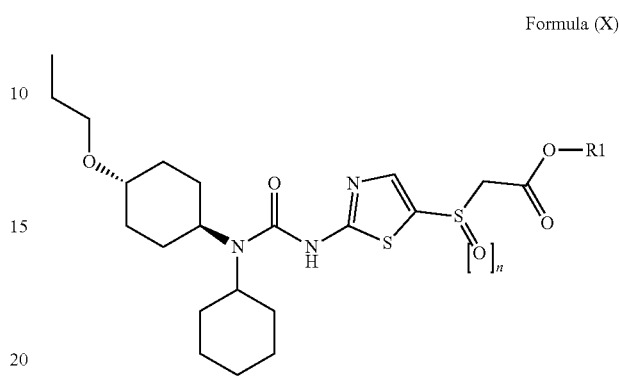

Formula (X)

wherein R1 is hydrogen, methyl, or ethyl, and n is 1 or 2, or a pharmaceutically acceptable salt thereof. In an embodiment, the present invention provides a compound of Formula (X), wherein R1 is hydrogen or ethyl and n is 1 or 2, or a pharmaceutically acceptable salt thereof. In another embodiment, the present invention provides a compound of Formula (X), wherein R1 is hydrogen and n is 1, or a pharmaceutically acceptable salt thereof. In another embodiment, the present invention provides a compound of Formula (X), wherein R1 is hydrogen and n is 2, or a pharmaceutically acceptable salt thereof.

Embodiments of the invention are directed to compounds of Formula (X) or a pharmaceutically acceptable salt thereof, wherein the particular compound has at least a particular percentage of purity. In some embodiments, the compound of Formula (X) or a pharmaceutically acceptable salt thereof is at least 80% pure, or at least 85% pure, or at least 90% pure, or at least 95% pure.

Embodiments of the invention are also directed to mixtures of compounds of Formula (X) or pharmaceutically acceptable salts thereof, wherein the mixture may comprise 1) between a detectable amount by ordinary analytical methods (such as by 1H NMR, solid state 13C NMR, XRPD, mid-IR (such as FT-IR), or near-IR techniques) and 1% of a first compound of Formula (X) or a pharmaceutically acceptable salt thereof and 2) the remainder is a second compound of Formula (X) or a pharmaceutically acceptable salt thereof. In another embodiment, the mixture of a compound of Formula (X) or pharmaceutically acceptable salts thereof comprises 1) between a detectable amount by ordinary analytical methods (such as by 1H NMR, solid state $^{13}$C NMR, XRPD, mid-IR (such as FT-IR), or near-IR techniques) and 2% of a first compound of Formula (X) or a pharmaceutically acceptable salt thereof and 2) the remainder is a second compound of Formula (X) or a pharmaceutically acceptable salt thereof.

In another embodiment, the present invention provides a compound wherein the compound is Sulfoxide-1

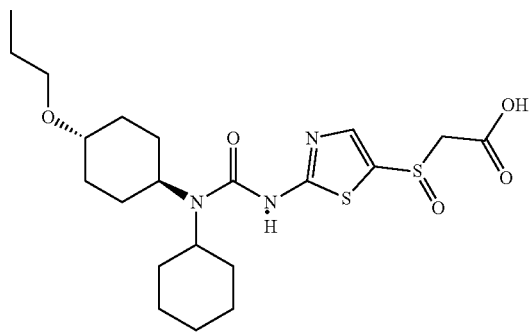

({2-[3-Cyclohexyl-3-(trans-4-propoxy-cyclohexyl)-ureido]-thiazol-5-ylsulfinyl}-acetic acid) or a pharmaceutically acceptable salt thereof.

In another embodiment, the present invention provides a compound wherein the compound is Sulfoxide-1A

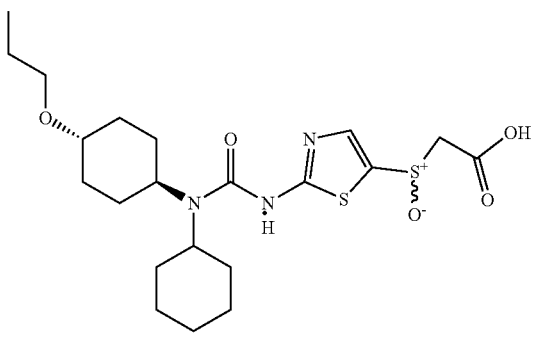

({2-[3-Cyclohexyl-3-(trans-4-propoxy-cyclohexyl)-ureido]-thiazol-5-ylsulfinyl}-acetic acid) or a pharmaceutically acceptable salt thereof, wherein the compound is enriched in one enantiomer or is a single enantiomer. In an embodiment, the present invention provides Sulfoxide-1A in percent enantiomeric excess (% ee) of greater than 50%, 75%, 90%, 95%, 97%, 98%, or 99%. In another embodiment, Sulfoxide-1A is the enantiomer where a solution of Sulfoxide-1A (20 mg/mL) in methanol with a % ee of >99.6% (as determined by chiral HPLC) rotates plane polarized light +12.61 degrees.

In another embodiment, the present invention provides a compound wherein the compound is Sulfoxide-1B

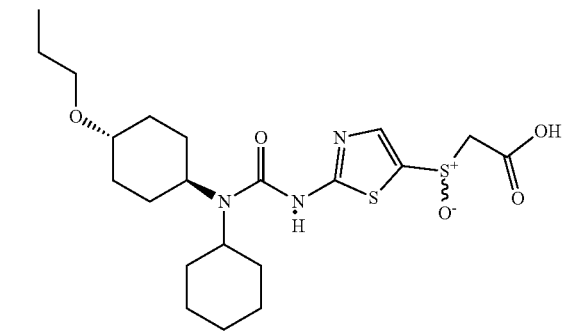

({2-[3-Cyclohexyl-3-(trans-4-propoxy-cyclohexyl)-ureido]-thiazol-5-ylsulfinyl}-acetic acid) or a pharmaceutically acceptable salt thereof, wherein the compound is enriched in one enantiomer or is a single enantiomer. In an embodiment, the present invention provides Sulfoxide-1B in enantiomeric excess of greater than 50%, 75%, 90%, 95%, 97%, 98%, or 99%. Sulfoxide-1B is the enantiomer where a solution of Sulfoxide-1B (20 mg/mL) in methanol with a % ee of >99.9% (as determined by chiral HPLC) rotates plane polarized light −12.5 degrees.

In another embodiment, the present invention provides (R)-{2-[3-Cyclohexyl-3-(trans-4-propoxy-cyclohexyl)-ureido]-thiazol-5-ylsulfinyl}-acetic acid or a pharmaceutically acceptable salt thereof.

In another embodiment, the present invention provides (S)-{2-[3-Cyclohexyl-3-(trans-4-propoxy-cyclohexyl)-ureido]-thiazol-5-ylsulfinyl}-acetic acid or a pharmaceutically acceptable salt thereof.

In another embodiment, the present invention provides a compound wherein the compound is Sulfone-1

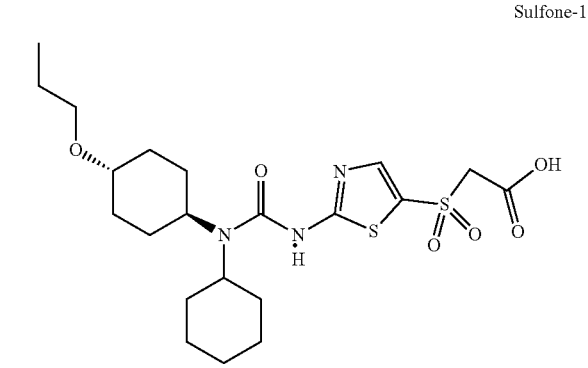

({2-[3-Cyclohexyl-3-(trans-4-propoxy-cyclohexyl)-ureido]-thiazol-5-ylsulfonyl}-acetic acid) or a pharmaceutically acceptable salt thereof.

The compound SM-1, an alkyl ester derivative, or pharmaceutically acceptable salt thereof may be an impurity in a compound of Formula (X) or pharmaceutically acceptable salt thereof left over from certain methods of synthesizing a compound of Formula (X) using SM-1, an alkyl ester derivative, or pharmaceutically acceptable salt. Conversely, compounds such as Sulfoxide-1 and Sulfone-1 may be degradation products resulting from the oxidation of SM-1. Thus, in another embodiment, the present invention provides a composition comprising SM-1 or a pharmaceutically acceptable salt thereof and a compound of Formula (X) wherein R1 is hydrogen, methyl, or ethyl, and n is 1 or 2, or a pharmaceutically acceptable salt of one or more of the foregoing compounds. In another embodiment, the present invention provides a composition comprising SM-1 or pharmaceutically acceptable salt thereof and one or more of Sulfoxide-1, Sulfoxide-1A, Sulfoxide 1-B, and Sulfone-1, or a pharmaceutically acceptable salt of one or more of the foregoing compounds.

In another embodiment, a compound of Formula (X) or pharmaceutically acceptable salt thereof described above may be a liver-selective glucokinase activator.

In another embodiment, the present invention provides a method of synthesizing a compound of Formula (X) wherein R1 is hydrogen, methyl, or ethyl, and n is 1 or 2, or a pharmaceutically acceptable salt of one or more of the foregoing compounds. Synthetic methods useful for preparing a compound of the invention are provided in the Examples section below. In an embodiment, a compound of Formula (X) may be prepared by oxidizing the compound SM-1 or by oxidizing an alkyl ester of SM-1 followed by the steps of a kinetic resolution and ester hydrolysis. In the reactions described in the Examples, it is also possible to make use of variants that are known to those of ordinary skill in this art.

III. Methods of Treatment

In another aspect, the present invention provides a method of treatment comprising administering to a subject in need thereof a compound of Formula (X) or a pharmaceutically acceptable salt thereof or a pharmaceutical composition comprising a compound of Formula (X) or a pharmaceutically acceptable salt thereof, wherein R1 is hydrogen, methyl, or ethyl, and n is 1 or 2. In an embodiment, for the compound of Formula (X), R1 is hydrogen, or ethyl and n is 1 or 2. In another embodiment, for the compound of Formula (X), R1 is hydrogen and n is 1. In another embodiment, for the compound of Formula (X), R1 is hydrogen and n is 2.

In another embodiment, the present invention provides a method of treatment comprising administering to a subject in need thereof Sulfoxide-1 or a pharmaceutically acceptable salt thereof or a pharmaceutical composition comprising Sulfoxide-1 or a pharmaceutically acceptable salt thereof, and a pharmaceutically acceptable carrier.

In another embodiment, the present invention provides a method of treatment comprising administering to a subject in need thereof Sulfoxide-1A or a pharmaceutically acceptable salt thereof or a pharmaceutical composition comprising Sulfoxide-1A or a pharmaceutically acceptable salt thereof and a pharmaceutically acceptable carrier, wherein Sulfoxide-1A or pharmaceutically acceptable salt thereof is enriched in one enantiomer or is a single enantiomer. In another embodiment, Sulfoxide-1A is administered in percent enantiomeric excess (% ee) of greater than 50%, 75%, 90%, 95%, 97%, 98%, or 99%.

In another embodiment, the present invention provides a method of treatment comprising administering to a subject in need thereof Sulfoxide-1B or a pharmaceutically acceptable salt thereof or a pharmaceutical composition comprising Sulfoxide-1B or a pharmaceutically acceptable salt thereof and a pharmaceutically acceptable carrier, wherein the Sulfoxide-1B or pharmaceutically acceptable salt thereof is enriched in one enantiomer or is a single enantiomer. In another embodiment, Sulfoxide-1B is administered in percent enantiomeric excess (% ee) of greater than 50%, 75%, 90%, 95%, 97%, 98%, or 99%.

In another embodiment, the present invention provides a method of treatment comprising administering to a subject in need thereof (R)-{2-[3-Cyclohexyl-3-(trans-4-propoxy-cyclohexyl)-ureido]-thiazol-5-ylsulfinyl}-acetic acid or a pharmaceutically acceptable salt thereof, or a pharmaceutical composition comprising (R)-{2-[3-Cyclohexyl-3-(trans-4-propoxy-cyclohexyl)-ureido]-thiazol-5-ylsulfinyl}-acetic acid or a pharmaceutically acceptable salt thereof, and a pharmaceutically acceptable carrier.

In another embodiment, the present invention provides a method of treatment comprising administering to a subject in need thereof (S)-{2-[3-Cyclohexyl-3-(trans-4-propoxy-cyclohexyl)-ureido]-thiazol-5-ylsulfinyl}-acetic acid or a pharmaceutically acceptable salt thereof, or a pharmaceutical composition comprising (S)-{2-[3-Cyclohexyl-3-(trans-4-propoxy-cyclohexyl)-ureido]-thiazol-5-ylsulfinyl}-acetic acid or a pharmaceutically acceptable salt thereof, and a pharmaceutically acceptable carrier.

In another embodiment, the present invention provides a method of treatment comprising administering to a subject in need thereof Sulfone-1 or a pharmaceutically acceptable salt thereof, or a pharmaceutical composition comprising Sulfone-1 or a pharmaceutically acceptable salt thereof, and a pharmaceutically acceptable carrier.

In another embodiment, the present invention provides a method of treatment comprising administering to a subject in need thereof a pharmaceutical composition comprising SM-1 and a compound of Formula (X) wherein R1 is hydrogen, methyl, or ethyl, and n is 1 or 2, or a pharmaceutically acceptable salt thereof, and a pharmaceutically acceptable carrier. In another embodiment, the present invention provides a method of treatment comprising administering to a subject in need thereof a pharmaceutical composition comprising SM-1 and one or more of Sulfoxide-1, Sulfoxide-1A, Sulfoxide 1-B, and Sulfone-1, or a pharmaceutically acceptable salt of any of the foregoing compounds and a pharmaceutically acceptable carrier.

In another embodiment, the amount of a compound of Formula (X) or a pharmaceutically acceptable salt thereof administered according to the methods of treatment herein may be from 0.05 mg to 1000 mg per day, or from about 1 mg to about 1000 mg per day, or from about 10 mg to about 1000 mg per day, or from about 100 mg to about 1000 mg per day. The compound of Formula (X) or a pharmaceutically acceptable salt thereof may be administered as a pharmaceutical composition in unit dosage form comprising between 0.05 mg and 1000 mg of Formula (X) or a pharmaceutically acceptable salt thereof.

In another embodiment, the present invention provides a method for the treatment of glucokinase-deficiency mediated conditions or diseases, or conditions benefiting from an increase in glucokinase activity, comprising administering to a subject in need of a compound or a pharmaceutical composition of the present invention.

In another embodiment, the present invention provides a method for treatment of metabolic disorders, for blood glucose lowering, for the treatment of hyperglycemia, for the treatment of hypoglycemia for the treatment of impaired glucose tolerance (IGT), for the treatment of Syndrome X, for the treatment of impaired fasting glucose (IFG), for the treatment of type 2 diabetes, for the treatment of type 1 diabetes, for delaying the progression of impaired glucose tolerance (IGT) to type 2 diabetes, for delaying the progression of non-insulin requiring type 2 diabetes to insulin requiring type 2 diabetes, for the treatment of dyslipidemia, for the treatment of hyperlipidemia, for the treatment of hypertension, for lowering of food intake, for appetite regulation, for the treatment of obesity, for regulating feeding behavior, or for enhancing the secretion of enteroincretins, comprising administering to a subject in need of such treatment a compound or a pharmaceutical composition of the present invention.

In another embodiment, the present invention provides a method for the preservation of beta-cell mass and function comprising administering to a subject in need of such treatment a compound or a pharmaceutical composition of the present invention.

In another embodiment, the present invention provides a method of treatment adjuvant to insulin in insulin-requiring diabetes type 2, or as replacement for insulin in insulin-requiring diabetes type 2 comprising administering to a subject in need of such treatment a compound or a pharmaceutical composition of the present invention.

In another embodiment, the present invention provides a method of delaying the onset of insulin requiring type 1 diabetes comprising administering to a subject in need of such treatment a compound or a pharmaceutical composition of the present invention.

In another embodiment, present the invention provides a method of preserving and/or increasing beta-cell mass and function in a subject having undergone pancreatic islet transplantation comprising administering to a subject in need of such treatment a compound or a pharmaceutical composition of the present invention.

In another embodiment, the present invention provides a method of improving liver function and/or survival in subjects undergoing liver transplantation comprising administering to a subject in need of such treatment a compound or a pharmaceutical composition of the present invention. In another embodiment, the present invention provides a method according wherein the administration occurs before, during or after transplantation, or any combination thereof.

In another embodiment, the present invention provides a method of preventing diabetic ketoacidosis or reducing the occurrence of diabetic ketoacidosis events in a subject comprising administering to a subject in need of such treatment a compound or a pharmaceutical composition of the present invention.

In another embodiment, the present invention provides a method of treating type 2 diabetes comprising administering to a subject in need thereof of a compound or a pharmaceutical composition according to the present invention. In an embodiment, the method comprises lowering a subject's HbA1c level by at least 0.1, 0.2, 0.3, 0.4, 0.5, 0.6, 0.7, 0.8, 0.9, 1.0% points. In another embodiment, the subject has a HbA1c level of at least 6.5%, 7.0%, 7.5%, 8.0%, 8.5%, or 9.0% prior to treatment.

In another embodiment, the present invention provides a method of treating type 1 diabetes comprising administering to a subject in need thereof of a compound or a pharmaceutical composition according to the present invention. In an embodiment, the method comprises lowering a subject's HbA1c level by at least 0.1, 0.2, 0.3, 0.4, 0.5, 0.6, 0.7, 0.8, 0.9, 1.0% points. In another embodiment, the subject has a HbA1c level of at least 6.5%, 7.0%, 7.5%, 8.0%, 8.5%, or 9.0% prior to treatment.

In another embodiment the present invention provides a method of treatment adjuvant to insulin in insulin-requiring diabetes type 2 or in diabetes type 1, or as replacement for insulin comprising administering to a subject in need of such treatment a compound according to the invention or pharmaceutical composition thereof.

In another embodiment, the present invention provides a method of preventing or delaying the onset of insulin dependence in a subject suffering from type 1 or type 2 diabetes by 1, 2, 3, 4, 5, 6, or 7 years comprising administering to a subject in need of such treatment a compound according to the invention or pharmaceutical composition thereof.

In another embodiment, the present invention provides a method of preserving and/or increasing beta-cell mass and function in patients having undergone pancreatic islet transplantation comprising administering to a subject in need of such treatment a compound according to the invention or pharmaceutical composition thereof.

In another embodiment the invention provides a method of preventing, reducing the likelihood of, or reducing the incidence of diabetic ketoacidosis comprising administering to a subject in need of such treatment a compound according to the invention or pharmaceutical composition thereof.

In another embodiment, the present invention provides the use of a compound according to the invention for increasing the activity of glucokinase.

In another embodiment, the present invention provides the use of a compound according to the invention for the preparation of a medicament for the treatment of metabolic disorders, for blood glucose lowering, for the treatment of hyperglycemia, for the treatment of hypoglycemia for the treatment of IGT, for the treatment of Syndrome X, for the treatment of impaired fasting glucose (IFG), for the treatment of type 2 diabetes, for the treatment of type 1 diabetes, for delaying the progression of impaired glucose tolerance (IGT) to type 2 diabetes, for delaying the progression of non-insulin requiring type 2 diabetes to insulin requiring type 2 diabetes, for the treatment of dyslipidemia, for the treatment of hyperlipidemia, for the treatment of hypertension, for lowering of food intake, for appetite regulation, for the treatment of obesity, for regulating feeding behavior, or for enhancing the secretion of enteroincretins. In another embodiment the invention provides the use of a compound according to the invention for the preparation of a medicament for the adjuvant treatment of type 1 diabetes for preventing the onset of diabetic complications.

In another embodiment, the present invention provides the use of a compound according to the invention for the preparation of a medicament for increasing the number and/or the size of beta cells in a mammalian subject, for treatment of beta cell degeneration, in particular apoptosis of beta cells, or for treatment of functional dyspepsia, in particular irritable bowel syndrome.

In another embodiment, the present invention provides any of the above uses in a regimen which comprises treatment with a further pharmaceutically active substance.

IV. Combination Treatment

In a further embodiment of the present invention, a compound of the invention may be administered in combination with one or more further active substances in any suitable ratios. Such further active agents may be selected from antidiabetic agents, antihyperlipidemic agents, antiobesity agents, antihypertensive agents and agents for the treatment of complications resulting from or associated with diabetes.

Suitable antidiabetic agents may include insulin, GLP-1 (glucagon like peptide-1) derivatives, and orally active hypoglycemic agents.

Suitable orally active hypoglycemic agents may include imidazolines, sulfonylureas, biguanides, meglitinides, oxadiazolidinediones, thiazolidinediones, insulin sensitizers, α-glucosidase inhibitors, agents acting on the ATP-dependent potassium channel of the pancreatic β-cells, GLP-1 agonists, DPP-IV (dipeptidyl peptidase-IV) inhibitors, PTPase (protein tyrosine phosphatase) inhibitors, inhibitors of hepatic enzymes involved in stimulation of gluconeogenesis and/or glycogenolysis, glucose uptake modulators, GSK-3 (glycogen synthase kinase-3) inhibitors, compounds modifying the lipid metabolism such as antihyperlipidemic agents and antilipidemic agents, compounds lowering food intake, and PPAR (peroxisome proliferator-activated receptor) and RXR (retinoid X receptor) agonists.

In another embodiment, a compound of the present invention may be administered in combination with a sulfonylurea such as tolbutamide, chlorpropamide, tolazamide, glibenclamide, glipizide, glimepiride, glicazide or glyburide.

In another embodiment, a compound of the present invention may be administered in combination with a biguanide such as metformin.

In another embodiment, a compound of the present invention may be administered in combination with a meglitinide, such as repaglinide or senaglinide/nateglinide.

In another embodiment, a compound of the present invention may be administered in combination with a thiazolidinedione insulin sensitizer such as troglitazone, ciglitazone, pioglitazone, rosiglitazone, isaglitazone, darglitazone, or englitazone.

In another embodiment, a compound of the present invention may be administered in combination with an α-glucosidase inhibitor such as voglibose, emiglitate, miglitol or acarbose.

In another embodiment, a compound of the present invention may be administered in combination with a glycogen phosphorylase inhibitor.

In another embodiment, a compound of the present invention may be administered in combination with an antihyperlipidemic agent or an antilipidemic agent such as cholestyramine, colestipol, clofibrate, gemfibrozil, lovastatin, pravastatin, simvastatin, probucol or dextrothyroxine.

In another embodiment, a compound of the present invention may be administered in combination with one or more antihypertensive agents. Examples of antihypertensive agents include 6-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin.

In another embodiment, a compound of the present invention may be administered in combination with insulin, insulin derivatives or insulin analogues.

In another embodiment the GLP-1 derivative to be employed in combination with a compound of the present invention refers to GLP-1(1-37), exendin-4(1-39), insulinotropic fragments thereof, insulinotropic analogues thereof and insulinotropic derivatives thereof.

In another embodiment, a compound of the present invention may be administered in combination with more than one of the above-mentioned compounds e.g. in combination with metformin and a sulphonylurea such as glyburide; a sulphonylurea and acarbose; nateglinide and metformin; acarbose and metformin; a sulfonylurea, metformin and troglitazone; insulin and a sulfonylurea; insulin and metformin; insulin, metformin and a sulfonylurea; insulin and troglitazone: insulin and lovastatin; etc.

Such other therapeutic agents may be administered by a like route or different route that the compound of the invention or a pharmaceutically acceptable salt thereof. Where a compound of the invention or a pharmaceutically acceptable salt thereof is used in combination with another therapeutic agent, the composition may contain the compound of the invention or a pharmaceutically acceptable salt thereof in combination with the other therapeutic agent(s). Alternatively, where separate dosage formulations are used, the compound of the invention or a pharmaceutically acceptable salt thereof and one or more additional therapeutic agents may be administered at essentially the same time (e.g., concurrently) or at separately staggered times (e.g., sequentially).

Any suitable combination of the compounds according to the invention with diet and/or exercise, one or more of the above-mentioned compounds and optionally one or more other active substances are within the scope of the present invention.

V. Pharmaceutical Compositions

In another aspect, the present invention provides a pharmaceutical composition comprising: a compound of Formula (X), wherein R1 is hydrogen, methyl, or ethyl, and n is 1 or 2, or a pharmaceutically acceptable salt thereof, and a pharmaceutically acceptable carrier. In an embodiment, R1 is hydrogen or ethyl and n is 1 or 2, or a pharmaceutically acceptable salt thereof. In another embodiment, R1 is hydrogen and n is 1, or a pharmaceutically acceptable salt thereof. In another embodiment, R1 is hydrogen and n is 2, or a pharmaceutically acceptable salt thereof.

In another embodiment, the present invention provides a pharmaceutical composition comprising a compound wherein the compound is Sulfoxide-1 or a pharmaceutically acceptable salt thereof, and a pharmaceutically acceptable carrier.

In another embodiment, the present invention provides a pharmaceutical composition comprising a compound wherein the compound is Sulfoxide-1A or a pharmaceutically acceptable salt thereof, wherein the compound is enriched in one enantiomer or is a single enantiomer, and a pharmaceutically acceptable carrier. In another embodiment, Sulfoxide-1A in the pharmaceutical composition is present in percent enantiomeric excess (% ee) of greater than 50%, 75%, 90%, 95%, 97%, 98%, or 99%.

In another embodiment, the present invention provides a pharmaceutical composition comprising a compound wherein the compound is Sulfoxide-1B or a pharmaceutically acceptable salt thereof, wherein the compound is enriched in one enantiomer or is a single enantiomer, and a pharmaceutically acceptable carrier. In another embodiment, Sulfoxide-1B in the pharmaceutical composition is present in percent enantiomeric excess (% ee) of greater than 50%, 75%, 90%, 95%, 97%, 98%, or 99%.

In another embodiment, the present invention provides a pharmaceutical composition comprising (R)-{2-[3-Cyclohexyl-3-(trans-4-propoxy-cyclohexyl)-ureido]-thiazol-5-ylsulfinyl}-acetic acid or a pharmaceutically acceptable salt thereof, and a pharmaceutically acceptable carrier.

In another embodiment, the present invention provides a pharmaceutical composition comprising (S)-{2-[3-Cyclohexyl-3-(trans-4-propoxy-cyclohexyl)-ureido]-thiazol-5-ylsulfinyl}-acetic acid or a pharmaceutically acceptable salt thereof, and a pharmaceutically acceptable carrier.

In another embodiment, the present invention provides a pharmaceutical composition comprising a compound wherein the compound is Sulfone-1 or a pharmaceutically acceptable salt thereof, and a pharmaceutically acceptable carrier.

The compound SM-1 or pharmaceutically acceptable salt thereof may be an impurity in a compound of Formula (X) left over from certain methods of synthesizing a compound of Formula (X) using SM-1. Conversely, compounds such as Sulfoxide-1 and Sulfone-1 may be degradation products resulting from the oxidation of SM-1. Thus, in another embodiment, the present invention provides a pharmaceutical composition comprising SM-1 or a pharmaceutically acceptable salt thereof and a compound of Formula (X) wherein R1 is hydrogen, methyl, or ethyl, and n is 1 or 2, or a pharmaceutically acceptable salt thereof, and a pharmaceutically acceptable carrier. In another embodiment, the present invention provides a pharmaceutical composition comprising SM-1 and one or more of Sulfoxide-1, Sulfoxide-1A, Sulfoxide 1-B, and Sulfone-1, or a pharmaceutically acceptable salt of any of the foregoing compounds and a pharmaceutically acceptable carrier.

In another embodiment, the present invention provides a pharmaceutical composition comprising a mixture of a compound of Formula (X) wherein R1 is hydrogen, methyl, or ethyl, and n is 1 or 2, or a pharmaceutically acceptable salt thereof and SM-1 or a pharmaceutically acceptable salt thereof, wherein the compound of Formula (X) or a pharmaceutically acceptable salt thereof is present in the pharmaceutical composition in an amount of less than 5 mg and SM-1 or a pharmaceutically acceptable salt thereof is present in the pharmaceutical composition in an amount between 10 mg to 1000 mg. In another embodiment, the compound of Formula (X) or a pharmaceutically acceptable salt thereof is present in the pharmaceutical composition in an amount between 0.0001 mg and 5 mg and SM-1 or a pharmaceutically acceptable salt thereof is present in the pharmaceutical composition in an amount between 50 mg to 500 mg.

In another embodiment, the present invention provides a pharmaceutical composition comprising a mixture of a compound of Formula (X) wherein R1 is hydrogen, methyl, or ethyl, and n is 1 or 2, or a pharmaceutically acceptable salt thereof and SM-1 or a pharmaceutically acceptable salt thereof, wherein the compound of Formula (X) or a pharmaceutically acceptable salt thereof is present in the pharmaceutical composition in an amount between 10 mg and 1000 mg and SM-1 or a pharmaceutically acceptable salt thereof is present in an amount of less than 5 mg. In another embodiment, the compound of Formula (X) or a pharmaceutically acceptable salt thereof is present in the pharmaceutical composition in an amount between 50 mg and 500 mg and SM-1 or a pharmaceutically acceptable salt thereof is present in the pharmaceutical composition in an amount between 0.0001 mg to 5 mg.

In another embodiment, the present invention provides a pharmaceutical composition comprising a mixture of Sulfoxide-1 or a pharmaceutically acceptable salt thereof and SM-1 or a pharmaceutically acceptable salt thereof. In a further embodiment, the pharmaceutical composition comprises between 10 mg and 1000 mg of SM-1 or a pharmaceutically acceptable salt thereof and less than 5 mg of Sulfoxide-1 or a pharmaceutically acceptable salt thereof. In another embodiment, the pharmaceutical composition comprises between a detectable amount (such as by 1H NMR, IR, or HPLC methods) to 5 mg of Sulfoxide-1 or a pharmaceutically acceptable salt thereof. In another embodiment, the detectable amount of Sulfoxide-1 may be between 0.0001 mg and 5 mg. In another embodiment, the detectable amount of Sulfoxide-1 may be at least 0.0001 mg, or at least 0.001 mg, or at least 0.01 mg, or at least 0.1 mg.

In another embodiment, the present invention provides a pharmaceutical composition comprising a mixture of Sulfone-1 or a pharmaceutically acceptable salt thereof and SM-1 or a pharmaceutically acceptable salt thereof. In a further embodiment, the pharmaceutical composition comprises between 10 mg and 1000 mg of SM-1 or a pharmaceutically acceptable salt thereof and less than 5 mg of Sulfone-1 or a pharmaceutically acceptable salt thereof. In another embodiment, the pharmaceutical composition comprises between a detectable amount (such as by 1H NMR, IR, or HPLC methods) to 5 mg of Sulfone-1 or a pharmaceutically acceptable salt thereof. In another embodiment, the detectable amount of Sulfone-1 may be at least 0.0001 mg, or at least 0.001 mg, or at least 0.01 mg, or at least 0.1 mg.

In another embodiment, the present invention provides a pharmaceutical composition comprising a mixture of Sulfoxide-1, Sulfone-1 and SM-1 or a pharmaceutically acceptable salt of any of the foregoing. In a further embodiment, the pharmaceutical composition comprises between 10 mg and 1000 mg of SM-1 or a pharmaceutically acceptable salt thereof and between 0.0001 mg to 5 mg of Sulfone-1 or a pharmaceutically acceptable salt thereof and between 0.0001 mg to 5 mg of Sulfoxide-1 or a pharmaceutically acceptable salt thereof.

The compounds of the present invention may be administered in either single or multiple doses. The pharmaceutical compositions according to the invention may be formulated with a pharmaceutically acceptable carrier as well as any other known adjuvants and excipients in accordance with conventional techniques such as those disclosed in Remington: The Science and Practice of Pharmacy, 19th Edition, Gennaro, Ed., Mack Publishing Co., Easton, PA, 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as hard or soft capsules, tablets, troches, dragees, pills, lozenges, powders and granules. Where appropriate, they can be prepared with coatings such as enteric coatings or they can be formulated so as to provide controlled release of the active ingredient such as sustained or prolonged release according to methods well known in the art.

Liquid dosage forms for oral administration include solutions, emulsions, aqueous or oily suspensions, syrups and elixirs.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. Depot injectable formulations are also contemplated as being within the scope of the present invention.

Other suitable administration forms include suppositories, sprays, ointments, cremes, gels, inhalants, dermal patches, implants etc.

A typical oral dosage may be in the range of from about 0.001 to about 100 mg/kg body weight per day, or from about 0.01 to about 50 mg/kg body weight per day, or from about 0.05 to about 10 mg/kg body weight per day administered in one or more dosages such as 1 to 3 dosages. In another embodiment, the typical oral dosage may be in the range of 1 mg to about 500 mg per dose, or from about 100 to about 500 mg per dose. The exact dosage will depend upon the frequency and mode of administration, the sex, age, weight and general condition of the subject treated, the nature and severity of the condition treated and any concomitant diseases to be treated and other factors evident to those skilled in the art.

Suitable pharmaceutical carriers may include inert solid diluents or fillers, sterile aqueous solution and various organic solvents. Examples of solid carriers include lactose, terra alba, sucrose, cyclodextrin, talc, gelatin, agar, pectin, acacia, magnesium stearate, stearic acid and lower alkyl ethers of cellulose. Examples of liquid carriers are syrup, peanut oil, olive oil, phospholipids, fatty acids, fatty acid amines, polyoxyethylene and water. Similarly, the carrier or diluent may include any sustained release material known in the art, such as glyceryl monostearate or glyceryl distearate, alone or mixed with a wax. The pharmaceutical compositions formed by combining the compounds of the present invention and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable carrier. Furthermore, the orally available formulations may be in the form of a powder or granules, a solution or suspension in an aqueous or non-aqueous liquid, or an oil-in-water or water-in-oil liquid emulsion.

Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules where the active ingredient is mixed with an inert solid diluent, for example, calcium carbonate, calcium phosphate or kaolin, or a soft gelatin capsules wherein the active ingredient is mixed with water or an oil medium, for example peanut oil, liquid paraffin, or olive oil.

If desired, the pharmaceutical composition of the present invention may comprise a compound according to the present invention in combination with further active substances such as those described in the foregoing.

VI. Assays

Glucokinase Activity Assay (I)

Glucokinase activity may be assayed spectrometrically using glucose 6-phosphate dehydrogenase to determine a test compound's activation of glucokinase. The final assay may contain 50 mM Hepes, pH 7.1, 50 mM KCl, 5 mM $MgCl_2$, 2 mM dithiothreitol, 0.6 mM NADP, 1 mM ATP, 0.195 µM G-6-P dehydrogenase, and 15 nM recombinant human glucokinase. The glucokinase is human liver glucokinase N-terminally truncated with an N-terminal His-tag and is expressed in E. coli as a soluble protein with enzymatic activity comparable to liver extracted GK.

The purification of His-tagged human glucokinase (hGK) may be performed as follows: The cell pellet from 50 mL E. coli culture is resuspended in 5 mL extraction buffer A (25 mM HEPES, pH 8.0, 1 mM $MgCl_2$, 150 mM NaCl, 2 mM mercaptoethanol) with addition of 0.25 mg/mL lysozyme and 50 µg/mL sodium azide. After 5 minutes at room temperature, 5 mL of extraction buffer B (1.5 M NaCl, 100 mM $CaCl_2$, 100 mM $MgCl_2$, 0.02 mg/mL DNase 1, a protease inhibitor tablet is added. The extract is then centrifuged at 15,000 g for 30 minutes. The resulting supernatant is loaded on a 1 mL Metal Chelate Affinity Chromatography (MCAC) column charged with $Ni^{2+}$. The column is washed with 2 volumes buffer A containing 20 mM imidazole and the bound his-tagged hGK is subsequently eluted using a 20 minute gradient of 20 to 500 mM imidazol in buffer A. Fractions are examined using SDS-gel-electrophoresis, and fractions containing hGK (MW: 52 KDa) are pooled. Finally, a gelfiltration step is used for final polishing and buffer exchange. hGK containing fractions are loaded onto a Superdex 75 (16/60) gelfiltration column and eluted with Buffer B (25 mM HEPES, pH 8.0, 1 mM $MgCl_2$, 150 mM NaCl, 1 mM Dithiothreitol). The purified hGK is examined by SDS-gel electrophoresis and MALDI mass spectrometry and finally 20% glycerol is added before freezing. The yield from 50 mL E. coli culture is generally approximately 2-3 mg hGK with a purity >90%.

The compound to be tested is added into the well in final 2.5% DMSO concentration in an amount sufficient to give a desired concentration of compound, for instance 1, 5, 10, 25 or 50 µM. The reaction starts after glucose is added to a final concentration of 2, 5, 10 or 15 mM. The assay may use a 96-well UV plate and the final assay volume used is 200 µl/well. The plate is incubated at 25° C. for 5 min and kinetics is measured at 340 nm in SpectraMax every 30 seconds for 5 minutes.

Results for each compound are expressed as the fold activation of the glucokinase activity compared to the activation of the glucokinase enzyme in an assay without compound after having been subtracted from a "blank", which is without glucokinase enzyme and without compound. A compound, which at a concentration of at or below 30 µM gives 1.5 fold higher glucokinase activity than the result from the assay without compound, is deemed to be an activator of glucokinase. The glucose sensitivity of the compounds may be measured at a compound concentration of 10 µM and at glucose concentrations of 5 and 15 mM.

Glucokinase Activity Assay (II)

Determination of Glycogen Deposition in Isolated Rat Hepatocytes:

Hepatocytes may be isolated from rats fed ad libitum by a two-step perfusion technique. Cells are be plated onto collagen-coated 96-well plates in basal medium (Medium 199 (5.5 mM glucose) supplemented with 0.1 µM dexamethasone, 100 units/mL penicillin, 100 mg/mL streptomycin, 2 mM L-glutamine and 1 nM insulin) with 4% FCS at a cell density of 30,000 cells/well. The medium is replaced with basal medium 1 hour after initial plating in order to remove dead cells. Medium is changed after 24 hours to basal medium supplemented with 9.5 mM glucose and 10 nM insulin to induce glycogen synthesis, and experiments are performed the next day. The hepatocytes are washed twice with prewarmed (37° C.) buffer A (117.6 mM NaCl, 5.4 mM KCl, 0.82 mM $Mg_2SO_4$, 1.5 mM $KH_2PO_4$, 20 mM HEPES, 9 mM $NaHCO_3$, 0.1% w/v HSA, and 2.25 mM $CaCl_2$), pH 7.4 at 37° C.) and incubated in 100 µl buffer A containing 15 mM glucose and increasing concentrations of a test compound (for instance 1, 5, 10, 25, 50 or 100 µM) for 180 minutes. Glycogen content may be measured using standard procedures (See, Agius, L. et al, Biochem J. 266, 91-102 (1990)). Results are expressed as percent increase in glycogen content. A compound that when used in this assay gives a significant increase in glycogen content compared to the result from the assay without compound is deemed to have activity in this assay.

Glucokinase Activity Assay (III)

Stimulation of Insulin Secretion by Glucokinase Activators in INS-1E Cells

The glucose responsive β-cell line INS-1E is cultivated as described by Asfari M et al., Endocrinology, 130, 167-178 (1992). The cells are then seeded into 96 well cell culture plates and grown to a density of approximately 5×104 per well. Stimulation of glucose dependent insulin secretion is tested by incubation for 2 hours in Krebs Ringer Hepes buffer at glucose concentrations from 2.5 to 15 mM with or without addition of glucokinase activating test compounds in concentrations of for instance 1, 5, 10, 25, 50 or 100 µM, and the supernatants collected for measurements of insulin concentrations by ELISA (n=4). A compound that when used in this assay gives a significant increase in insulin secretion in response to glucose compared to the result from the assay without that test compound is deemed to have activity in this assay.

Caco-2 Permeability

Differentiated Caco-2 cells form a polarized epithelial cell monolayer that provides a physical and biochemical barrier to the passage of ions and small molecules. Using commercially available kits, the Caco-2 monolayer may be used as an in vitro model of the human small intestinal mucosa to predict the intestinal permeability or absorption of orally administered drugs. Researchers have shown a correlation for some molecules between the in vitro apparent permeability (Papp) across Caco-2 monolayers and the in vivo fraction absorbed.

The permeability of a compound may be evaluated in a bi-directional transport experiments at multiple concentrations (such as 1, 2, 5, 20, 100 and 200 µg/mL) using Caco-2 monolayers. The apparent permeability coefficients ($P_{app}$) for a compound may be calculated and compared with the permeability of a high permeability marker (such as labetalol) and a low permeability marker (such as mannitol).

Efflux Substrate Activity and Transporter Inhibition

The cell-based bidirectional permeability assay (or monolayer efflux assay) is a method for determining transporter inhibition (such as P-glycoprotein (P-gp) or Breast Cancer Resistance Protein (BCRP)) potential of test compounds in drug discovery. The experimental protocol for this assay is well established and typically, bidirectional permeability of a known substrate is assessed alone and in the presence of a single concentration of test compound to estimate the inhibition potential.

The monolayer efflux assay, where the ratio of basolateral-to-apical (B→A) permeability versus apical-to-basolateral (A→B) permeability is compared with a value of 1, is regarded as the standard for identifying substrates. Due to concentration-dependent inhibition of active efflux on the apical side by inhibitors, the B→A permeability decreases whilst A→B permeability increases with ratio approaching unity as the dose of inhibitor increases. The affinity of inhibitor to efflux protein(s) may be studied by calculating the active flux that can be obtained from the B→A fluxes in the absence and presence of efflux inhibitors. Inhibition potency, determined by inhibitor concentration-dependent transport assay, is usually represented as an IC50 value, the concentration that gives 50% of maximum inhibition of a known P-gp or BCRP substrate. Specificity of the inhibitor to P-gp or BCRP may be determined by competitive assays, which involve a transport assay of a known substrate in the presence of known inhibitors (specific to various transporters) with and without test compounds. Thus, appropriate design of competitive inhibition assays using known selected substrates and modulators will show the specificity of an inhibitor towards an efflux pump.

P-Glycoprotein

The potential for P-glycoprotein (P-gp) substrate inhibitory activity of a test compound may be evaluated by determining a test compound's Caco-2 permeability in the presence or absence of a P-gp inhibitor such as Cyclosporin A (CsA) or verapamil.

The potential inhibitory activity of a compound on the P-gp transporter expressed on Caco-2 cell monolayers may be investigated in experiments monitoring the bi-directional transport of a test compound in the presence or absence of a P-gp inhibitor such as Cyclosporin A (CsA) or verapamil.

The potential inhibitory activity of a compound on the P-gp transporter expressed on Caco-2 cell monolayers may also be investigated in experiments monitoring the bi-directional transport of [$^3$H]-digoxin in the presence of increasing concentrations of a test compound (such as 1, 5, 20, 100, and 200 µg/mL or 1.6, 3.2, 16, 32, 160 and 320 µg/mL). If the efflux of [$^3$H]-digoxin is not inhibited by a test compound, the test compound is likely a poor inhibitor of P-gp. If the efflux of [$^3$H]-digoxin is inhibited by a test compound, the IC50 value may be calculated using a non-linear regression of permeability data collected at various concentrations.

Breast Cancer Resistance Protein

The substrate and inhibitor potential of a test compound for the apical efflux transported breast cancer resistance protein (BCRP) may also be evaluated using a bidirectional permeability assessment where the controls are Ko143 (a potent inhibitor of BCRP) and E3S (estrone-3-sulphate, a substrate for BCRP) and across a range of test compound concentrations such as 1, 5, 20, 100, and 200 µg/mL or 1.6, 3.2, 16, 32, 160 and 320 µg/mL).

While the invention has been described and illustrated with reference to certain preferred embodiments thereof, those skilled in the art will appreciate that various changes, modifications and substitutions can be made therein without departing from the spirit and scope of the present invention.

EXAMPLES

Example 1—Preparation of Racemic Sulfoxide Ester-1

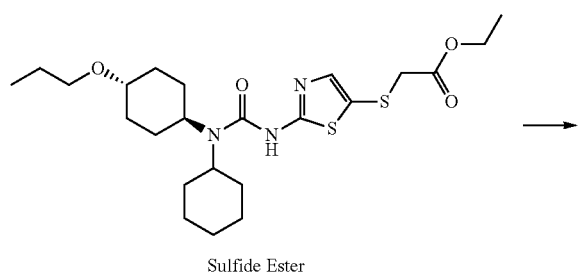

Sulfide Ester

The Sulfide Ester starting material may be prepared according to procedures provided in WO 2005/066145, Example 368.

mCPBA (5.95 g, 26.5 mmol, 1.05 eq) was added portion wise to a stirred solution of Sulfide Ester (10.0 g, 20.7 mmol) in DCM (100 mL) at zero degrees. After 30 min at zero degrees, the reaction mixture was slowly warmed to room temperature and stirred for an additional two hrs. The mixture was quenched with aqueous $NaHCO_3$ and extracted with DCM. The combined organic layer was washed with more $NaHCO_3$ and brine before drying and evaporating. The crude racemic Sulfoxide Ester-1 was purified via column chromatography eluted with 30% EtOAc-Hexanes to afford (8.69 g, 17.39 mmol).

Example 2—Kinetic Resolution

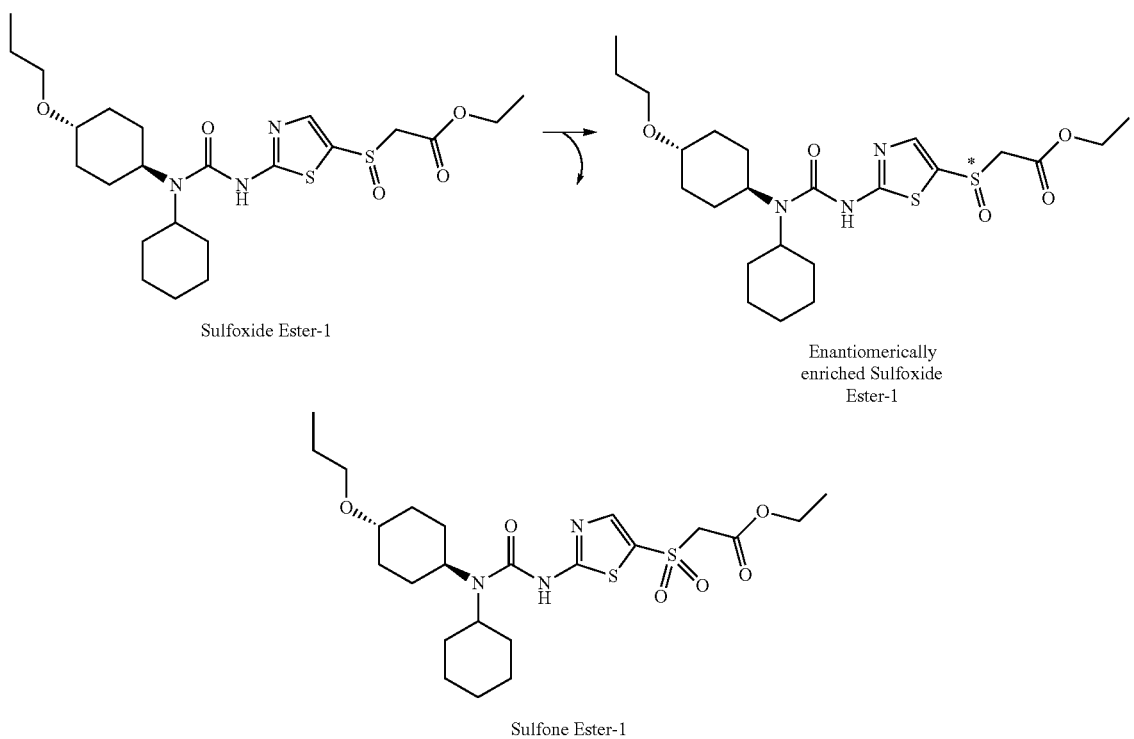

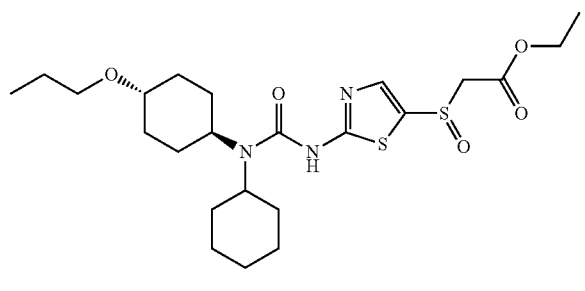

Sulfoxide Ester-1

To a DCM (20 mL) solution of (R)-binaphthol (1 mmol, 0.1 eq) was introduced $Ti(O-i-Pr)_4$ (0.5 mmol, 0.05 eq) and $H_2O$ (10 mmol) using a syringe under ambient atmosphere at room temperature. After the resulting brown solution was stirred magnetically at that same temperature for 1 hr, the racemic Sulfoxide Ester-1 (10 mmol, 5 g) was introduced using a syringe at 25° C. After 0.5 hr, 70% aqueous TBHP (10 mmol, 1 eq) was introduced using a syringe, and the mixture was stirred for 3 days (monitored using chiral HPLC for the formation of the Sulfone Ester-1 and disappearance of one enantiomer). The reaction mixture was directly submitted to column chromatography (eluent using 30-40% EtOAc-Hexanes) to afford both the Sulfone Ester-1 and enantiomerically enriched Sulfoxide Ester-1. The ee (~97%) of the recovered Sulfoxide Ester-1 was determined by chiral HPLC. The yield for the enantiomerically enriched Sulfoxide Ester-1 and the Sulfone Ester-1 was about 39% and 41%, respectively.

Example 3—Preparation of Sulfoxide-1A or Sulfoxide-1B

To a solution of enantiomerically enriched Sulfoxide Ester-1 (3 g, 6 mmol) from Example 2 in 30 mL of THF was added aqueous NaOH [2N] (12 mmol, 6 mL) at 0° C. The reaction mixture was slowly warmed to room temperature for 30 min, then the TH F was evaporated.

Water was added before the addition of HCl [2M] solution and adjusted to pH of 2. The mixture was filtered, and the collected solid was rinsed with water before drying at 50° C. overnight.

The free acid was re-dissolved via a minimum amount of EtOAc at 60° C. before slowly cooling to room temperature for crystallization overnight. Re-crystallization was performed two or three times to afford an enantiomer of Sulfoxide-1 in enantiomeric excess of over 99%. Using a procedure similar to Examples 2 and 3 and (S)-binaphthol in place of (R)-binaphthol, one of skill in the art may prepare the opposite enantiomer in greater that 99% ee

Example 4—Preparation of Sulfone-1

Sulfone-1 was synthesized by hydrolyzing Sulfone Ester-1. To a solution of Sulfone Ester-1 in THF, aqueous NaOH [2N] was added at 0° C. The reaction mixture was warmed to room temperature for 30 min, then the THF was evaporated.

Water was added before the addition of HCl [2M] solution and adjusted to pH of 2. The mixture was filtered, and the collected solid was rinsed with water before drying at overnight.

Example 5—Solubility Data

The aqueous solubility of Sulfoxide-1, Sufloxide-1A, Sulfoxide-1B, Sulfone-1, and SM-1 was investigated. As shown in Table 1 below, Sulfoxide-1, Sufloxide-1A, Sulfoxide-1B, and Sulfone-1 exhibited much greater aqueous solubility than SM-1 across a range of pH's.

TABLE 1

| | Solubility (µg/mL) | | | | |
|---|---|---|---|---|---|
| | Sulfone-1 | Sulfoxide-1 | Sulfoxide-1A | Sulfoxide-1B | SM-1 |
| 0.1N HCl | 10 | 30 | 120 | 120 | Not Detected |
| Acetate Buffer pH 4.5 | 2070 | 2570 | 1630 | 1850 | 0.44 |
| Phosphate Buffer pH 6.5 | 2100 | 2930 | 1940* | 1990* | 21 |

Example 6—Caco-2 Permeability and Efflux Substrate Activity

The Caco-2 permeability, P-gp substrate and inhibitory activity, and BCRP substrate and inhibitory activity of Sulfoxide-1, Sufloxide-1A, Sulfoxide-1B, Sulfone-1, and SM-1 was investigated using procedures similar to those described above.

As summarized in Table 2 below, except for Sulfoxide-1B, all of the tested compounds had low Caco-2 cell permeability and were weak efflux transporter substrates at the tested concentrations of 12.5 µg/mL and 50 µg/mL. Sulfoxide-1B had moderate Caco-2 cell permeability and was not an efflux transporter substrate at the tested concentrations of 12.5 µg/mL and 50 µg/mL.

TABLE 2

| Caco-2 Permeability and Efflux Substrate Activity | | | | | |
|---|---|---|---|---|---|
| | Sulfone-1 | Sulfoxide-1 | Sulfoxide-1A | Sulfoxide-1B | SM-1 |
| Caco-2 Permeability | Low | Low | Low | Moderate | Low |
| Efflux Transporter Substrate | Yes | Yes | Yes | No | Yes |

As summarized in Table 3 below, Sulfone-1 and Sulfoxide-1 exhibit similar P-gp inhibitory activity with a P-gp $IC_{50}$ of about 100 µg/mL, and Sulfoxide-1B was the weakest P-gp inhibitor among the tested compounds. Sulfone-1, Sulfoxide-1 and Sulfoxide-1B were the weakest BCRP inhibitors, and SM-1 was the strongest BCRP inhibitor of the tested compounds.

TABLE 3

| Transporter Inhibition | | | | | |
|---|---|---|---|---|---|
| | Sulfone-1 | Sulfoxide-1 | Sulfoxide-1A | Sulfoxide-1B | SM-1 |
| P-gp $IC_{50}$ (µg/mL) | ≈100 | ≈100 | ≈65 | >100 | 52.3 |
| BCRP $IC_{50}$ (µg/mL) | >100 | >100 | ≈80 | >100 | 8.9 |

What is claimed is:

1. A compound of Formula (X)

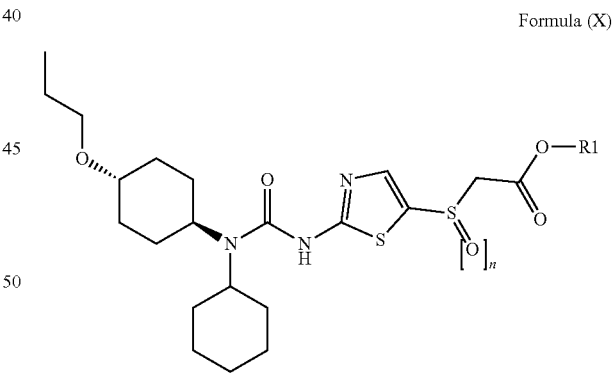

Formula (X)

wherein R1 is hydrogen, methyl, or ethyl, and n is 1 or 2, or a pharmaceutically acceptable salt thereof.

2. The compound of claim 1, wherein R1 is hydrogen or ethyl and n is 1 or 2, or a pharmaceutically acceptable salt thereof.

3. The compound of claim 1, wherein the compound is (R)-{2-[3-cyclohexyl-3-(trans-4-propoxy-cyclohexyl)-ureido]thiazol-5-ylsulfinyl} acetic acid or a pharmaceutically acceptable salt thereof.

4. The compound of claim 1, wherein the compound is(S)-{2-[3-cyclohexyl-3-(trans-4-propoxy-cyclohexyl)-ureido]thiazol-5-ylsulfinyl} acetic acid or a pharmaceutically acceptable salt thereof.

5. The compound of claim 1, wherein the compound is {2-[3-cyclohexyl-3-(trans-4-propoxy-cyclohexyl)-ureido]thiazol-5-ylsulfinyl} acetic acid or a pharmaceutically acceptable salt thereof.

6. A pharmaceutical composition comprising a compound of claim 1 and a pharmaceutically acceptable carrier.

7. The pharmaceutical composition of claim 6, wherein R1 is hydrogen or ethyl and n is 1 or 2, or a pharmaceutically acceptable salt thereof.

8. The pharmaceutical composition of claim 6, wherein the compound is (R)-{2-[3-cyclohexyl-3-(trans-4-propoxy-cyclohexyl)-ureido]thiazol-5-ylsulfinyl}-acetic acid or a pharmaceutically acceptable salt thereof.

9. The pharmaceutical composition of claim 6, wherein the compound is(S) {2-[3-cyclohexyl-3-(trans-4-propoxy-cyclohexyl)-ureido]thiazol-5-ylsulfinyl}-acetic acid or a pharmaceutically acceptable salt thereof.

10. The pharmaceutical composition of claim 6, wherein the compound is {2-[3-cyclohexyl-3-(trans-4-propoxy-cyclohexyl)-ureido]thiazol-5-ylsulfonyl}-acetic acid or a pharmaceutically acceptable salt thereof.

11. A pharmaceutical composition comprising:
{2-[3-cyclohexyl-3-(trans-4-propoxy-cyclohexyl)-ureido]-thiazol-5-ylsulfanyl} acetic acid or a pharmaceutically acceptable salt thereof; and
a compound of Formula (X)

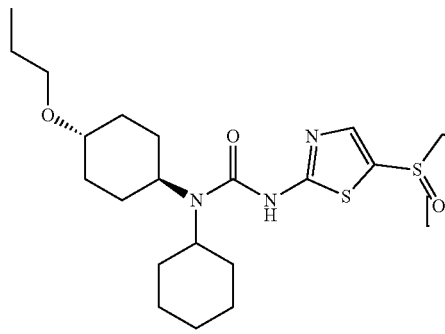

Formula (X)

wherein R1 is hydrogen, methyl, or ethyl, and n is 1 or 2, or a pharmaceutically acceptable salt thereof;
and a pharmaceutically acceptable carrier.

12. The pharmaceutical composition of claim 11, comprising
{2-[3-Cyclohexyl-3-(trans-4-propoxy-cyclohexyl)-ureido]thiazol-5-ylsulfanyl}-acetic acid or a pharmaceutically acceptable salt thereof; and
{2-[3-Cyclohexyl-3-(trans-4-propoxy-cyclohexyl)-ureido]thiazol-5-ylsulfinyl}-acetic acid or a pharmaceutically acceptable salt thereof.

13. The pharmaceutical composition of claim 11, comprising
{2-[3-Cyclohexyl-3-(trans-4-propoxy-cyclohexyl)-ureido]thiazol-5-ylsulfanyl}-acetic acid or a pharmaceutically acceptable salt thereof; and
{2-[3-Cyclohexyl-3-(trans-4-propoxy-cyclohexyl)-ureido]thiazol-5-ylsulfonyl}-acetic acid or a pharmaceutically acceptable salt thereof.

14. The pharmaceutical composition of claim 11, comprising
{2-[3-Cyclohexyl-3-(trans-4-propoxy-cyclohexyl)-ureido]thiazol-5-ylsulfanyl}-acetic acid or a pharmaceutically acceptable salt thereof; and
(R)-{2-[3-Cyclohexyl-3-(trans-4-propoxy-cyclohexyl)-ureido]thiazol-5-ylsulfinyl}-acetic acid or a pharmaceutically acceptable salt thereof.

15. The pharmaceutical composition of claim 11, comprising
{2-[3-Cyclohexyl-3-(trans-4-propoxy-cyclohexyl)-ureido]thiazol-5-ylsulfanyl}-acetic acid or a pharmaceutically acceptable salt thereof; and
(S)-{2-[3-Cyclohexyl-3-(trans-4-propoxy-cyclohexyl)-ureido]thiazol-5-ylsulfinyl}-acetic acid or a pharmaceutically acceptable salt thereof.

16. A method of treating of type 1 or type 2 diabetes comprising:
administering to a subject in need thereof a compound of Formula (X)

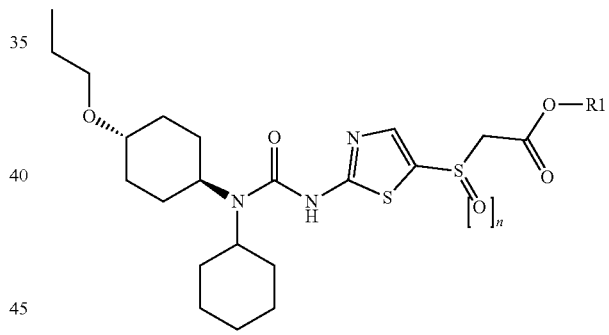

Formula (X)

wherein R1 is hydrogen, methyl, or ethyl, and n is 1 or 2, or a pharmaceutically acceptable salt thereof.

17. The method of claim 16, wherein the subject has an HbA1c of at least 7%.

* * * * *